US009696315B2

(12) United States Patent
Wang et al.

(10) Patent No.: US 9,696,315 B2
(45) Date of Patent: Jul. 4, 2017

(54) METHOD AND COMPOSITION FOR A PROTEIN TRANSDUCTION TECHNOLOGY AND ITS APPLICATIONS

(71) Applicant: Wayne State University, Detroit, MI (US)

(72) Inventors: Jianjun Wang, Troy, MI (US); Qianqian Li, Troy, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 14/261,627

(22) Filed: Apr. 25, 2014

(65) Prior Publication Data

US 2014/0342389 A1 Nov. 20, 2014

Related U.S. Application Data

(63) Continuation of application No. 12/128,320, filed on May 28, 2008, now Pat. No. 8,722,348.

(51) Int. Cl.

| | |
|---|---|
| ***G01N 33/58*** | (2006.01) |
| ***C12N 15/88*** | (2006.01) |
| ***G01N 33/50*** | (2006.01) |
| ***C12P 21/00*** | (2006.01) |
| ***G01N 33/68*** | (2006.01) |

(52) U.S. Cl.

CPC ............. *G01N 33/58* (2013.01); *C12N 15/88* (2013.01); *C12P 21/00* (2013.01); *G01N 33/5023* (2013.01); *G01N 33/68* (2013.01); *G01N 2458/15* (2013.01)

(58) Field of Classification Search

CPC ...................................................... C12N 15/88

See application file for complete search history.

(56) References Cited

U.S. PATENT DOCUMENTS

| | | | | |
|---|---|---|---|---|
| 4,666,828 | A | 5/1987 | Gusella | |
| 4,683,202 | A | 7/1987 | Mullis | |
| 4,801,531 | A | 1/1989 | Frossard | |
| 5,192,659 | A | 3/1993 | Simons | |
| 5,272,057 | A | 12/1993 | Smulson et al. | |
| 5,880,103 | A | 3/1999 | Urban et al. | |
| 6,407,178 | B1 | 6/2002 | Kolbe et al. | |
| 6,783,751 | B2 | 8/2004 | Heumann | |
| 2003/0134352 | A1 | 7/2003 | Freimuth et al. | |
| 2004/0142474 | A1* | 7/2004 | Mahato et al. | 435/458 |
| 2004/0185528 | A1 | 9/2004 | Horn et al. | |
| 2005/0064545 | A1 | 3/2005 | DeMarco et al. | |
| 2005/0074840 | A1 | 4/2005 | Brondyk et al. | |
| 2005/0215474 | A1 | 9/2005 | Oaks et al. | |

FOREIGN PATENT DOCUMENTS

| | | |
|---|---|---|
| WO | WO-02/22174 | 3/2002 |
| WO | WO-2005026196 | 3/2005 |
| WO | WO-2008050255 | 5/2008 |

OTHER PUBLICATIONS

Hung, et al. International J of Pharmaceutics, 2005, 289:197-208.*
Zelphati et al. JBC, 2001, 276(37):35103-35110.*
Futami et al. J of Biosecience and Bioengineering, 2005, 99(2):95-103.*
Aridor, Meir et al. Traffic Jam: A Compendium of Human Diseases that Affect Intracellular Transport Processes, Traffic. Toolbox 1:836-851 (2000).
Ausubel et al. Biology, Green Publishing Associate. Brooklyn, NY, 1988.
Ausubel et al., Current Protocols in Molecular Biology, John Wiley and Sons, Baltimore, Maryland (1989).
Ausubel, et al. (1987 and Supplements) Short Protocols in Molecular Biology, Wiley & Sons Inc., New York.
Birren et al (eds) Genome Analysis: A Laboratory Manual Series. vols. 1-4 Cold Spring Harbor Laboratory-Press, New York (1998).
Brock et al., Biology of Microorganisms, 5th Edition, Prentice Hall, New Jersey (1988).
Burz, David S. et al., Mapping Structural Interations Using In-Cell NMR Spectroscopy (STINT-NMR), http://www.nature.com/naturemethods, 2006.
Cai et al. "An efficient and cost-effective isotope labeling protocol for proteins expressed in *Escherichia coli*", J of Biomolecular NMR, 1998, 11:97-102.
Chang et al. "Cellular internalization of fluorescent proteins via arginine-rich intracellular delivery peptide in plant cells", Plant Cell Physiol. 2005, 46(3):482-488.
Crowe et al., (1992) QIAexpress: The High Level Expression & Protein Purification System QUIAGEN, Inc. Chatsworth, CA.
Demain et al. (Eds), Manual of Industrial Microbiology and Biotechnology, American Society for Microbiology, Washington D.C. (1986).

(Continued)

*Primary Examiner* — Bin Shen
(74) *Attorney, Agent, or Firm* — Dinsmore & Shohl LLP

(57) ABSTRACT

A protein transduction method for efficiently delivery of exogenous proteins into mammalian cells is invented, which has the capability of targeting different cellular compartments and protection from degradation of the delivered proteins from cellular proteases. A composition for treat proteins has cation reagents, lipids and enhancers in a carrier. The method can be used in a number of ways including: production of large quantities of properly folded, post-translationally modified proteins using mammalian cell machinery, a in-cell fluorescence spectroscopy and imaging using small molecule fluorophores and a in-cell NMR spectroscopy using living mammalian cells. The method permits cell biology at atomic resolution that is physiologically and pathological relevant and permits protein therapy to treat human diseases. The method can also be used to deliver exogenous protein inside mammalian cells, wherein the exogenous proteins follow a similar secretion pathway as that of the endogenous protein.

14 Claims, 13 Drawing Sheets

(56) References Cited

OTHER PUBLICATIONS

Deutscher (1990) "Guide to Protein Purification" in Methods in Enzymology, vol. 182.
Dobson, Christopher M. Protein Folding and Misfolding, University of Cambridge, 2003.
Futami et al. "Intracellular delivery of proteins into mammalian living cells by polyethyenimine-cationization", J of Biosci. & bioeng., 2005, 99(2):95-103.
Gerhardt et al. (Eds). Methods for General and Molecular Biology, American Society for Microbiology, Washington D.C. (1994).
Guignet et al. "Reversible site-selective labeling of membrane proteins in live cells", Nature Biotechnolgy, 2004, 22(4):440-444.
Hochuli (1989) "Guide to Protein Purification" in Methods in Enzymology, vol. 182.
Hochuli (1990) "Purification of Recombinant Proteins with Metal Chelate Absorbent" in Setlow (ed.) Genetic Engineering, Principle and Methods 12:87-98. Plenum Press, N.Y.
Innis, et al. (eds.)(1990) PCR Protocols: A Guide to Methods and Applications Academic Press, N.Y.
Kumagal et al. "Absorptive-mediated endocytosis of cationized albumin and a beta-endorphin-cationized albumin chimeric peptide by isolated brain capillaries", JBC, 1987, 262(31):15214-15219.
Li et al. "Real Time investigation of protien folding, structure, and dynamics in living cells", Methods in Cell Biology,2008, 90:287-326.
Maniatis, et al. (1982) Molecular Cloning, A Laboratory Manual, Cold Spring Harbor Laboratory, Cold Spring Harbor Press.
Melamed, et al. (1990) Flow Cytometry and Sorting Wiley-Liss, Inc., New York, N.Y.
Mishell and Shiigi (eds), Selected Methods in Cellular Immunology, W.H. Freeman and Co., New York (1980).
PCR Protocols: A Guide to Methods and Applications, Academic Press, San Diego, CA (1990).
Perbal, A Practical Guide to Molecular Cloning, John Wiley & Sons, New York (1988).
Prochiantz, Alain. For Protein Transduction, Chemistry Can Win Over Biology, Nature Methods, vol. 4, No. 2 (2007).
Robinson, et al. (1993) Handbook of Flow Cytometry Methods Wiley-Liss, New York, N.Y.
Sambrook et al., Molecular Cloning: A Laboratory Manual, Cold Spring Harbor Labortory Press, New York (1989).
Sambrook, et al. (2001) Molecular Cloning: A Laboratory Manual, (3rd ed.). vols. 1-3, CSH Press, NY.
Shapiro (1988) Practical Flow Cytometry Liss, New York, N.Y.
Stites et al.(eds), Basic and Clinical Immunology (8th Edition), Appleton & Lange, Norwalk, CT (1994).
Testoni et al. 1996. Blood 87.3822.
Wang et al. "Arginine-rich intracellular delivery peptides noncovalently transport protein into living cells", BBRC, 2006, 346:758-767.
Watson et al, Recombinant DNA. Scientific American Books. New York, (1992).
Woodford et al. (Eds). Molecular Bacteriology: Protocols and Clinical Applications, Humana Press, Totowa, N.J. (1998).

* cited by examiner

Bacterial Expressed LBD - apoER2
↓
Modified LBD - apoER2
↓ QQ1 (Less Toxicity)
Incubate with Modified LBD - apoER2
↓ 2 Hours, Hela Cells
↓ ( LBD - apoER2 Loading)
Exchange Incubation Medium
(No modified LBD _apoER2)
↓ 2 - 5 hours (Folding)
Lysis Cells
↓
Purification
↓
Far Western Blot
(anti apoE/RAP antibody)
From 1.5 mg bacterial expressed
LBD - apoER2, we obtained 0.5 - 0.8 mg
refolded LBD - apoER2

METHOD AND COMPOSITION FOR A PROTEIN TRANSDUCTION TECHNOLOGY AND ITS APPLICATIONS

REFERENCE TO RELATED APPLICATION

This application is a divisional of U.S. patent application Ser. No. 12/128,320, filed May 28, 2008, the entire content of which is incorporated herein by reference.

BACKGROUND OF THE INVENTION

1. Technical Field

The present invention relates to protein transduction and uses thereof. More specifically, the present invention relates to protein transduction reagents that enable proteins to be delivered into mammalian cells and how to uses of the protein transduction technology, including in vivo protein folding, trafficking, secretion pathways of transduced exogenous proteins, production of large quantities of native folded, post-translationally modified proteins, in-cell structural biology and protein therapy.

2. Description of the Related Art

Proteins are necklaces of amino acids, long chain molecules. Proteins are the most important molecules inside every living cell, tissue, organ within the human body. Proteins are involved in virtually all aspects of life. Proteins control thinking, they regulate all physiological reactions, they metabolize carbohydrates and fats that bodies use, they defend bodies against bacteria and viruses, and they work as enzymes, hormones, antibodies, cytokines and signaling molecules that transmit information into cells. As enzymes, they are the driving force behind all of the biochemical reactions. As structural elements, they are the main constituent of bones, muscles, hair, skin and blood vessels. As antibodies, they recognize invading elements and allow the immune system to eliminate the unwanted invaders. While scientists have sequenced the human genome, how proteins work largely remains a mystery. This is because in order for proteins to function (e.g. as enzymes or antibodies), the protein must take on a particular shape, also known as a "fold". If the protein does not fold correctly, disease and dysfunction occur. Some examples of which include, but are not limited to, Alzheimer's disease, Huntington's disease, cystic fibrosis, BSE (Mad Cow disease), an inherited form of emphysema, and even many cancers. When proteins misfold, they can clump together ("aggregate"). These clumps can often gather in the brain, where they are believed to cause the symptoms of Mad Cow or Alzheimer's disease.

When proteins fold inside a cell, they are frequently subjected to various amounts of spatial confinement. In many cases, proteins are folded in the endoplasmic reticulum ("ER"), which is a membrane-containing cellular compartment that contains many proteins at specific concentrations. Proteins can be encapsulated inside helper molecules, called chaperones and folding, enzymes. These chaperones are involved with helping proteins fold inside cells. Therefore, protein folding inside the cell is quite different from its folding in the test tube. However, current studies of protein folding are mainly in the test tube. Although significant advance has been achieved, these results of protein folding in the test tube have to be verified in living cells and such a technique of study protein folding in the living cell is lacking.

The study of protein structure has received a major boost recently with the increasing amount of structures being deposited on the Protein Data Bank (PDB) on a daily basis, but these structures are typically not determined in viva, but in artificial crystals and solutions. Over the past five decades, X-ray crystallography and the resulting atomic models of proteins and nucleic acids have contributed greatly to an understanding of structural, molecular, and chemical aspects of biological phenomena. Currently, X-ray crystallography is a mature high-resolution structural biology tool that can be used to quickly determine protein structures. However, X-ray crystallography requires high quality single crystal of proteins in order to do x-ray diffraction and this is not always achievable. In contrast, another high-resolution structural biology tool, nuclear magnetic resonance (NMR), has been developed since 1980s. This technique only requires protein in solution at 50 μM to 1 mM concentrations. This technique also provides protein dynamics information via NMR relaxation measurements. Although NMR is a less mature high-resolution structural tool, it provides an alternative high-resolution structural biology technique, allowing for determination of protein structures at atomic resolution.

When these methods cannot be used, computer-based protein modeling techniques have been used with some success. These modeling techniques use the known three-dimensional structure of a homologous protein to approximate the structure of another protein. This is not an accurate method because the actual structure is not known, but is approximated.

Fluorescence spectroscopy is another structural technique, which can be used to obtain structural information. The well-developed Forster resonance energy transfer (FRET) technique can be used to measure the distance between fluorescence donor and acceptor, and can thus provide important information about protein folding and structure. However, FRET can only provide one distance from one pair of fluorescence donor and acceptor each time. To determine a protein structure, hundreds to thousands of distances within a protein are necessary to determine protein structure at atomic resolution. This requires enormous amount of work, including mutagenesis, protein production, fluorescence labeling and FRET measurement of every pair of fluorescence donor and acceptor. The FRET measurement can also be obtained in the living cells since the introduction of Green/Red Fluorescence Protein (GFP/RFP) technique. The in vivo FRET measurement is widely used to study protein-protein and domain-domain interactions, however, the distance measurement between GFP and RFP seems to be meaningless, since both GFP and RFP are proteins of 25-28 kDa. Thus, the current in vivo FRET measurement cannot be used to obtain accurate information about protein structure and folding. Therefore, fluorescence spectroscopy is not considered to be a viable high-resolution structural biology tool.

Fluorescence imaging is a technique that is routinely used to study protein location and trafficking in living cells. Currently, this technique extensively utilizes GFP technique, which fuses GFP in either the N- or the C-terminal end of a protein. Using a confocal microscope, the GFP-labeled protein can be visualized for their locations and trafficking inside the cells. However, it is unknown whether the GFP fusion changes the location of the protein of interest inside the cells. Thus, extensive control experiments have to be carried out. Even with these control experiments, sometimes the situation inside the cells is complex and no definite conclusion can be made using fluorescence imaging.

Currently, there is no available means for detecting high-resolution protein structure in living cells. However, it is critical for scientists to verify if the in vitro determined protein structures are the same as the structures of these proteins in living cells. An in-cell structural biology is necessary to push the current cell biology to atomic resolution and no such technology is currently available. In addition, this in-cell structural biology will allow us to combine cell biology techniques with high-resolution structural biology techniques, thus to accurately correlate protein structural information with cellular functions.

Using bacteria to produce recombinant proteins opens the door of modern molecular biology. Indeed, bacterial expression enables us to utilize the recombinant DNA technique to produce large quantities of recombinant proteins. When bacterial cells are used to overexpress exogenous proteins, the recombinant protein is often sequestered in bacterial cell inclusion bodies. For the recombinant proteins to be useful, they must be purified from the inclusion bodies. During the purification process, the recombinant proteins are denatured and must then be re-natured. Denatured protein is commonly refolded in vitro by diluting the denaturant away. Protein unfolding normally induces a hydrophobic collapse that may cause protein aggregation. In vitro protein refolding results in the protein shielding its hydrophobic patches in the core of the molecule. Unfortunately, during the in vitro refolding process, proteins do not always form the native bioactive conformation. Two competing processes occur: refolding and aggregation. It is suggested that the driver for protein aggregation is hydrophobic amino acids exposed at the surface. Aggregation is undesirable and reduces the yield of functional, native protein.

Bacterial cells cannot be used to produce many proteins due to misfolding of these proteins in the bacterial cells. In addition, bacterial cells do not contain complex machinery for protein post-translational modification. However, protein post-translational modifications are critical for the biological functions of many proteins. Thus, the bacterial expressed recombinant proteins are not the same as the native proteins and are not functional. For production of native proteins, mammalian cells must be used. Unlike bacterial expression, the yield of mammalian cell protein expression is much lower and costly. A new technology of production of large quantities of properly folded, post-translationally modified proteins is definitely necessary for modern biology and medical sciences.

The impermeable nature of the cell membrane to peptide, protein, DNA and RNA limits the therapeutic potential of these "information-rich" biological molecules and prevents the uptake of the in vitro labeled macromolecules by cells for structural biology studies in the living cell at atomic resolution. However, a new, non-invasive protein transduction technology is emerging, following the discovery of the cell penetrating peptide (CPP) that is successfully used to efficiently transport heterogeneous bioactive cargo into the cell in an unconventional way. The protein transduction technology in vivo to deliver bioactive cargo into various tissues of living animals has been reported. This novel technology opens up many new possibilities for intracellular delivery of therapeutic macromolecules for treatment of human diseases or for intracellular transduction of labeled macromolecules for structural biology studies in living cells, thus potentially pushing cell biology to atomic resolution.

Despite these notable successes, the use of protein transduction technology has yet to become commonplace in cell biology and in therapeutic applications. Several major challenges lay in front of this new technology that prevent it to be widely used in many fields of biomedical sciences. The first challenge is the fate or secretion pathway of delivered exogenous proteins using protein transduction technology. It is still unknown how the exogenous proteins traffic inside cells after being delivered into cells. The famous Blobel's "Signal Theory" guides the fate of endogenous protein to traffic inside the cells, and thus dictates the subcellular locations of endogenous proteins. Questions have arisen regarding whether the exogenous proteins follow the same secretion pathway as that of the endogenous proteins. These questions have to be addressed for physiological and pathological relevance of protein transduction technology. The second major challenge is lack of delivery specificity of the current protein transduction agents, specifically, in terms of targeting to specific cell types and specific cell compartments. Indeed, the current protein transduction reagents are not "smart" enough to specifically deliver exogenous proteins into a targeting tissue type or cellular compartment.

Most human diseases are related to the malfunctioning of particular proteins, either systemically or locally. Therapeutic proteins, including native and engineered proteins, can be used as highly effective medical treatments (protein therapy) for a wide array of diseases in which the protein is either lacking or deficient (growth hormone and insulin), or the therapeutic protein is used to inhibit a biological process (antibodies that block blood supply to tumors). In contrast to gene therapy, protein therapy uses well-defined, precisely structured proteins, with previously defined optimal doses of the individual protein for disease states, and with well-known biological effects. However, an obstacle currently hinders protein therapy as a treatment of human diseases. This obstacle is the mode of delivery: oral, intravenous, intra-arterial, or intramuscular routes of administration are not always as effective as desired. In most cases, the therapeutic protein is metabolized or cleared before it even reaches the target tissue. To make protein therapy possible, an efficient delivery system of protein is required to ensure that therapeutic protein is stable and able to deliver to the target tissues for treatment of the diseases.

SUMMARY OF THE INVENTION

The present invention is a method for protein transduction into mammalian cells and the applications of this protein transduction method. The method can be used for the production of large quantity of native folded, post-translationally modified proteins using mammalian cell folding/post-translational modification machinery. The method can also be used for studies of protein folding, structure, interactions and trafficking in living mammalian cell, using in-cell fluorescence spectroscopy and imaging and in-cell NMR spectroscopy.

The present invention can also be used to develop the physiologically and pathologically relevant, atomic resolution cell biology and protein therapy to treat human diseases.

The QQ series protein transduction reagent of the present invention can efficiently deliver proteins into mammalian cell, making this method possible.

A composition of QQ reagents for treating proteins having cation reagents, lipids, and enhancers in a carrier is provided. Accordingly, the amount of modification of target protein with QQ reagents can be adjusted by altering the compositions to obtain the best protein transduction efficiency. The composition enable proteins to be delivered into mammalian cells and properly fold and post-translationally modified.

The method of the present invention can also include a labeling step, either NMR or fluorescence labeling, that includes labeling the protein prior to QQ reagent modification. The labeling enables better viewing of the protein within cells using high-resolution biophysical methods.

The method can be used in a number of ways including: production of large quantities of properly folded, post-translationally modified proteins using mammalian cell machinery, a in-cell fluorescence spectroscopy and imaging using small molecule fluorophores and a in-cell NMR spectroscopy using living mammalian cells. The method permits cell biology at atomic resolution that is physiologically and pathological relevant and protein therapy to treat human diseases.

The method can also be used to deliver exogenous protein inside mammalian cells, wherein the exogenous proteins follow a similar secretion pathway as that of the endogenous protein.

These and other objects, advantages and features of the invention will be more fully understood and appreciated by reference to the description of the current embodiment and the drawings.

DESCRIPTION OF THE INVENTION

Figure 1:
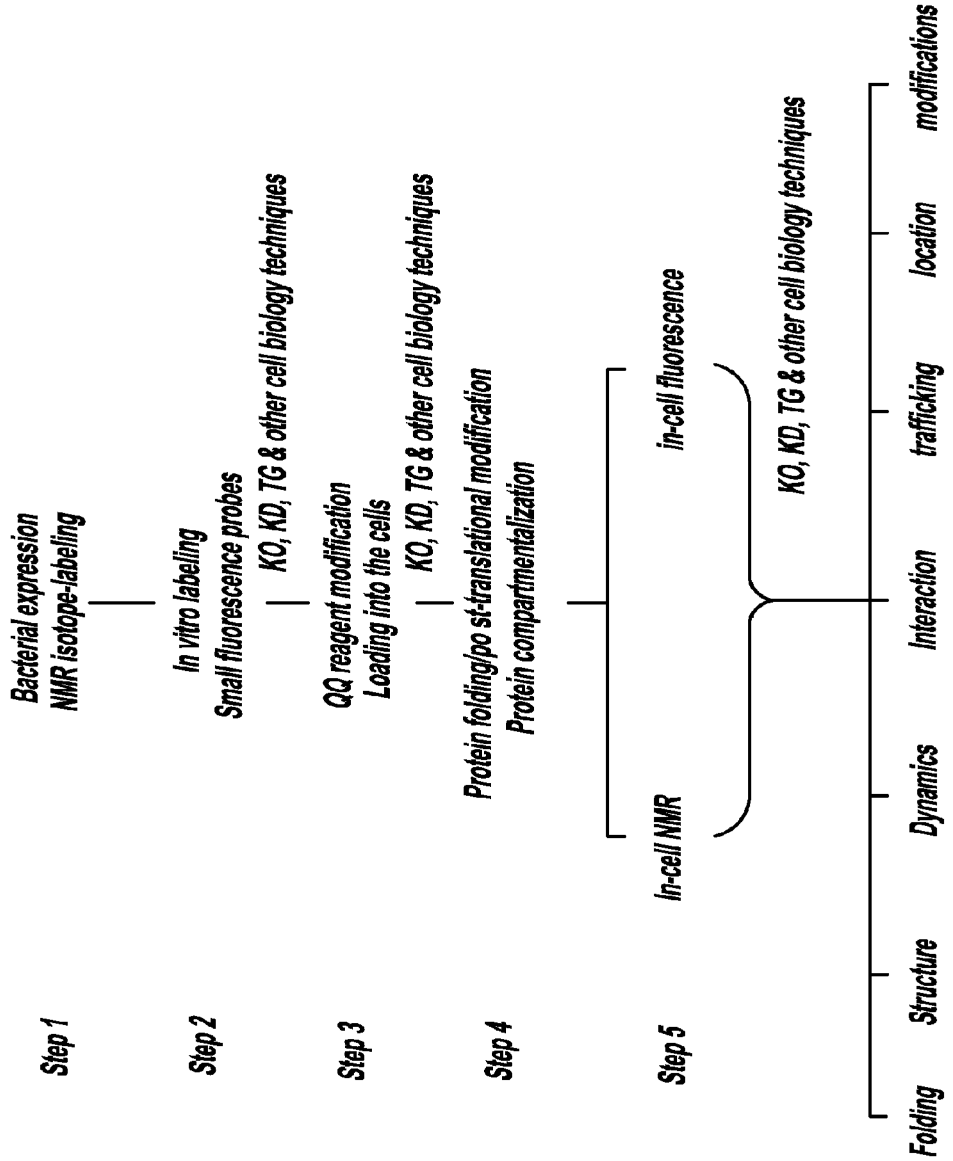
FIG. 1 is a flow chart depicting the method of the present invention, showing a simple step of utilization of the QQ reagents.

The present invention provides the QQ series of protein transduction reagents (QQ reagents) that can be used to deliver protein into any mammalian cells. In contrast to the currently available protein transduction reagents, such as protein transduction domain ("PTB") or cell penetrating peptide ("CPP"), the QQ reagents have an ability to deliver high concentrations of proteins into mammalian cells (up to 50-200 μM). Utilization of QQ reagents is very simple, only requiring incubation of the protein of interest with the QQ reagent, passing the protein solution through a quick-spin column to separate QQ reagent modified protein from free QQ reagents and another incubation with cells. QQ reagents are safe to the cells since the majority of the compositions of the QQ reagents are food additives that have been proved by FDA. More importantly, QQ reagents have two special features that other currently available protein transduction reagents do not have: QQ reagents can target different cell compartment and QQ reagents can protect protein of interest from degradation by proteases.

In contrast to the other protein transduction reagents currently available, such as PTB or CPP, QQ reagents have the following features that are unique and novel and distinctly different from the other protein transduction reagents:

(1) A non-invasive protein transduction method that is applicable to any mammalian cells.
(2) A high protein transduction efficiency method (50-200 μM protein delivery into the cells).
(3) A method that has the capability of targeting specific cell compartments or cell organelles.
(4) The QQ series reagents can either non-covalently or covalently associate with protein (a unique feature) and dissociate from the protein inside of cells. Thus, the protein under investigation is not functionally altered.
(5) The QQ series reagents are food additives that has been approved by FDA, having no or little cellular toxicity.
(6) The QQ series reagent protects proteins from protease degradation inside the cells.
(7) The application of QQ reagent is very simple and only requires a step of incubation with cells. No any other step, such as molecular cloning like CPP/PTB, is necessary.
(8) The QQ series reagent enables multiple proteins to be delivered into cells simultaneously or consecutively.

The reagents of the present invention can be used in numerous applications, such as to: (1) utilize cell folding machinery to properly fold bacterial expressed protein; (2) utilize cell post-translational modification machinery to properly post-translationally modify bacterially expressed proteins; (3) investigate the secretion pathways of the exogenous proteins that are delivered into the cell by the QQ reagents; (4) investigate the degradation of the exogenous proteins that are delivered into the cell by the QQ reagents; (5) study protein-protein interaction in living cells; and (6) study protein function at a cellular level. The reagent can also be used for the following: (1) Protein Therapy using the QQ reagent to target cellular compartment; and (2) physiologically and pathologically relevant, atomic resolution cell biology.

The present invention demonstrates that the exogenous bacterial expressed protein, after being delivered into mammalian cells, follows the same secretion pathway as the endogenous proteins. This discovery provides a foundation for future applications of protein transduction technology, including protein therapy and atomic resolution cell biology.

The present invention also provides a method that enables production of large quantity of native folded, post-translationally modified proteins using mammalian cell folding and post-translational modification machinery. The method uses bacteria to produce recombinant protein that is then modified with the QQ reagent and delivered into mammalian cells. The mammalian cell machinery will fold and post-translationally modify the transduced protein to produce native functional proteins that can be purified from the cells with affinity column which can bind to the tag (His-tag or other tags) introduced into recombinant proteins. The efficiency of recovery of recombinant protein from mammalian cell was about 30-60%.

The term "proteins" as used herein is intended to include any of a group of complex organic macromolecules that contain carbon, hydrogen, oxygen, nitrogen, and usually sulfur and are composed of one or more chains of amino acids. Proteins are fundamental components of all living cells and include many substances, such as enzymes, hormones, and antibodies that are necessary for the proper functioning of an organism. Examples of proteins tested include, but are not limited to: plasma protein (human apolipoprotein AI, human apolipoprotein E and mouse apolipoprotein AI), ER residence protein (mouse MESD(1-195) and Receptor Associate Protein (RAP)), receptor protein (the ligand-binding domain of human apoE receptor 2 (LBD-apoER2) and the YWTD β-propeller/EGF domains of LRP6, membrane protein mouse PMP22). These proteins have different hydrophobic and hydrophilic characters.

A "modified protein" is a protein that has been treated with the QQ reagent of the present invention. The QQ reagent enables the protein to function normally while the protein is delivered into cells.

The term "folding" as used herein is the process whereby a protein molecule assumes its intricate three-dimensional structure. The process of folding in vivo often begins co-translationally, so that the N-terminus of the protein begins to fold while the C-terminal portion of the protein is still being synthesized by the ribosome.

The term "post-translational modification" as used herein is the process whereby, after translation, a protein molecule get modified covalently at certain amino acids in several different ways, such as glycosylation, phosphorylation and ubiqutilization. Post-translational modifications usually occur in the ER and the Golgi of the mammalian cells.

The term "cell machinery" as used herein is intended to mean the machinery within a cell that is used by that cell for protein folding and for post-translational modification of the proteins produced by that cell.

The method of the present invention includes the steps of expressing a protein using bacteria, labeling the protein with probes, modification of the protein with the QQ reagents, incubation of the modified protein with mammalian cells and protein folding and post-translational modification of the protein within cells. First, the protein is expressed in bacteria. Optionally, the bacterial expressed protein can be labeled with NMR and fluorescence probes. The bacterial expressed protein is then modified using the QQ reagents of the present invention. The protein can then be delivered into mammalian cells by incubation of the QQ reagent modified protein with mammalian cells for several hours. The normal cell machinery can then properly fold and post-translationally modify the transduced protein for production of the native fold, post-translationally modified, functional proteins which can be purified using an affinity column.

The method enables analysis of the protein folding process in any cells, including both bacterial and mammalian cells. The method also enables studies of both protein structure and dynamics in the living cell, since this method allows one to label the protein in vitro and then transduce the labeled protein into mammalian cells for high-resolution biophysical studies, including in-cell NMR and in-cell fluorescence. Finally, the method of the present invention enables a combination of atomic resolution structural biology techniques with cell biology techniques (KO/TG and NMR/fluorescence). The method can thus be used to study structural biology at atomic resolution levels. In other words, structural biology can be studied at a physiologically and pathologically relevant level. By enabling such a study the method allows for utilization of cell biology techniques, such as knockout, transgenic and knockdown techniques, along with high-resolution structural biology.

The method of the present invention can be used to test drugs to determine how they affect protein folding. A "screen" can be used to determine if the drug being used has potential problems with regard to creating improper protein folding. As a screen, the method enables problems to be uncovered early in the developmental stages, to provide better analysis with regard to potential side effects of a medication.

The ability of this system to deliver multiple proteins simultaneously or consecutively can be applied to test protein-protein interactions and metabolic pathway interferences.

In-cell NMR and in-cell fluorescence techniques can also be developed to study protein structure/folding/trafficking/interactions within living cells. The high transduction efficiency at 50-200 μM concentrations inside cells makes in-cell NMR possible. In addition, the ability of QQ reagents to target different cell compartments, where the reaction occurs, ensures the physiological/pathological relevance of both in-cell NMR and in-cell fluorescence studies. As stated above, once the protein has been labeled, modified, and transferred into mammalian cells, the protein can be monitored to identify relevant mechanisms, changes, trafficking and interactions. This is beneficial on a number of levels. First, it provides input as to the specific mechanisms involved with protein and specifically protein folding. Second, it provides information with regard to the interactions surrounding proteins and protein folding, since there are so many diseases that are related to improper folding. It is critical to determine all cellular components that are involved with the folding process. Third, it provides the ability to visualize the actual 3D structure of the protein, once folded, inside cells.

The method of the present invention can also be used to deliver therapeutic proteins into tissues/cells for treatment of the diseased tissue/cells using protein therapy. The special ability of targeting different cell compartments by QQ reagents enables protein therapy to become a functional treatment option. Since the method enables proteins to be modified, transferred into a cell and targeted at a specific cell compartment, the protein can be used to alter the cell functions. For example, a modified protein can be transferred into a cell in need of treatment and since the method of the present invention utilizes the existing cellular folding machinery, the cell will fold the protein and thus the protein will be incorporated into the cell. As listed above, many diseases are known to be directly related to improper protein folding. For example, more than 50% of natural occurring mutants of LDL receptor are so-called class 2 mutants that remain in the ER and Golgi due to either misfolding or partially folded. These mutants are associated with Familiar Hypercholesterolemia (FH)—an autosomal dominant disorder affecting about 1 in 500 individuals worldwide. Patients with homozygotes develop severe atherosclerosis at a very early age. Knockdown of the LDLR mutation expression with supplement having wild-type LDLR using QQ protein transduction technology may rescue these patients. Therefore, bypassing the existing disease-causing mutant proteins and adding a correct protein, diseases can be treated in a safe and effective manner.

Protein therapy is similar to gene therapy but instead of inserting genes into the cells genome, proteins can be delivered into cells for treatment. In a manner similar to gene therapy, protein therapy enables targeted treatment of cells with specific proteins. For example, there are numerous diseases that impact either protein production or the manner of protein folding. By inserting properly folded proteins into cells or tissues, the cells or tissues can be treated so that they are no longer in a disease state. Protein therapy has previously been impossible because proteases in blood and within the cells digest the delivered proteins. In order for protein therapy to be practical, the delivered protein has to be protected inside the cell from protosomes. The QQ reagent of the present invention protects the protein from degradation and thus enables the protein to be inserted into a cell as part of a protein therapy.

The reagent of the present invention is a reagent that enables a protein to be transferred into a mammalian cell. The reagent includes cation reagents, a lipid, and an enhancer. One example of an appropriate cation reagent is polyethylenimine (M.W.: 600 Da, 2,000 Da and 25,000 Da). The lipid can be any lipid known to those of skill in the art to have the same general properties as those listed herein. Examples of such lipids include, but are not limited to, DOTAP, DOPE, POPC, and DMPE. The enhancers can be any enhancer that significantly enhances cell loading of cationized proteins. Examples of such enhancers in cell cultures include, but are not limited to MG132, protease inhibitor, $CaCl_2$, DMSO, growth factors and $Na_2HCO$. Other enhancers can also be used, including, but not limited to, cell membrane surfactants. The reagent can also include stabilizers and other inert carriers that do not affect the function of the reagent. As shown in Table 1 in the Examples, the concentrations and specific compounds utilized can vary.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Methods:

General Methods in Molecular Biology:

Standard molecular biology techniques known in the art and not specifically described are generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series, Vols.* 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

Some of the standard methods are described or referenced, e.g., in Maniatis, et al. (1982) Molecular Cloning, A Laboratory Manual, Cold Spring Harbor Laboratory, Cold Spring Harbor Press; Sambrook, et al. (1989) Molecular Cloning: A Laboratory Manual, (2d ed.), vols 1-3, CSH Press, NY; Ausubel, et al., Biology, Greene Publishing Associates, Brooklyn, N.Y.; or Ausubel, et al. (1987 and Supplements) Current Protocols in Molecular Biology, Greene/Wiley, New York; Innis, et al. (eds.)(1990) PCR Protocols: A Guide to Methods and Applications Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in Methods in Enzymology, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, N.Y.; and Crowe, et al. (1992) QIAexpress: The High Level Expression & Protein Purification System QUIAGEN, Inc., Chatsworth, Calif.

FACS analyses are described in Melamed, et al. (1990) Flow Cytometry and Sorting Wiley-Liss, Inc., New York, N.Y.; Shapiro (1988) Practical Flow Cytometry Liss, New York, N.Y.; and Robinson, et al. (1993) Handbook of Flow Cytometry Methods Wiley-Liss, New York, N.Y.

General Methods in Microbiology

Standard microbiology techniques known in the art and not specifically described were generally followed as in Gerhardt et al. (Eds), Methods for General and Molecular Biology, American Society for Microbiology, Washington D.C. (1994), and in Woodford et al. (Eds), Molecular Bacteriology: Protocols and Clinical Applications, Humana Press, Totowa, N.J. (1998) and in Demain et al. (Eds), Manual of Industrial Microbiology and Biotechnology, American Society for Microbiology, Washington D.C. (1986), and in Brock et al., Biology of Microorganisms, 5.sup.th Edition, Prentice Hall, New Jersey (1988).

General Methods in Immunology:

Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Example 1

Experimental Methods

Reagents:

Polyethylenimine (PEI) 600, 1200, 2,000 (2K), 8,000 (8K), 12,000 (12K), 25,000 (25K), and 60,000 (60K) are purchased from Sigma-Aldrich. Lipids: DOTAP, DOPE, POPC and DMPE are purchased from Avanti polar lipids, Inc.

Enhancer: MG132 protease inhibitor cocktail are purchased from Sigma-Aldrich. DMSO, $CaCl_2$, growth factor and $Na_2HCO$ are also purchased from Sigma-Aldrich. The addition of these enhancers significantly enhanced cell loading of cationized proteins.

Other enhancers can be used, including cell membrane surfactants. These materials can be purchased from Fisher.

Protease inhibitor Cocktail is purchased from Sigma (Cat# P1860).

Antibodies:

Goat anti-apoE poly-Ab and mouse anti apoE mono-Ab are purchased from Chemicon international. Anti LRP8 mono-Ab is purchased from Abnova Corporation. Goat anti 6×His-tag poly-Ab is purchased from Innovative Research. Anti RAP 7F1 is purchased from Innovative Research.

Anti goat IgG peroxidase conjugated is purchased from Sigma. Anti Rabbit and anti Mouse IgG peroxidase conjugated are purchased from Bio-Rad.

Cell Lines:

Hela cell line, GM 001300 cell line, BHK-570 cell line, CHO cell line, Raw cell line, MCF7 cell line, and HEK-293T cell line.

Recipes for QQ Series Reagents:

Stock Solutions:

Stock solutions of the following reagents are prepared as follows:

Cation Reagents: Stock Solution

| 600 | 1.2K | 2K | 8K | 12K | 25K | 60K |
|---|---|---|---|---|---|---|
| 50 mg/ml | 20 mg/ml | 50 mg/ml | 20 mg/ml | 20 mg/ml | 50 mg/ml | 50 mg/ml |

was dissolved in water and pH adjusted to 3.7-4.5 using HCl

Lipids:

| DOTAP | DOPEPOPC | DMPE | |
|---|---|---|---|
| 1 mg/ml | 1 mg/ml | 1 mg/ml | 1 mg/ml |

Enhancers:

| MG132 | $CaCl_2$ | $Na_2HCO$ | DMSO |
|---|---|---|---|
| 1 mM | 1M | 1M | 0.1M |

For different experiments one can choose different combinations of QQ reagents, e.g. to observe protein trafficking and location, QQ1 can be used which have the least cell toxicity. QQ1 can be used to incubate protein for few days without causing significant cell death. For protein folding and post-translational modification, it requires maximum loading in a short period of time, QQ8-QQ10 may be used, which have a higher cell toxicity. However, cells survive with proper functions in a short period of incubation time, such as 4-8 hours.

However, protein modified with 60K seems to give the best transfer efficiency. Protein modified with 2K alone only give intermediate transfer efficiency.

Protein Modifications with QQ reagents.

Proteins of interest are first dissolved into sodium phosphate buffer (pH7.0, NaCl 50 mM) at concentrations of 0.5-10 mg/ml, depends on protein solubility. Protein solubility was found to influence cationization efficiency. To completely dissolve proteins, an overnight stir of the protein solution at room temperature is performed (with or without DTT at 3 mM for overnight, depending on if the protein of interest has Cysteine residues).

A lipid DOTAP/DOPE (1:1) emulsion was prepared using a method as the following: 1 mg of DOTAP/DOPE (0.5 mg:0.5 mg=1:1) mixture was dissolved in chloroform and dried under $N_2$ gas. The dried lipid film was then dissolved in PBS buffer, p1-17.0 and the lipid solution was sonicated for 3×30 seconds using a power of 7-8 on a sonicator from Fisher Scientific (Sonic Dismembrator, Model 100) with micro probe. The lipid solution was further incubated at 37° C. for 2 hours until the suspension becomes semi-clear. The prepared emulsion was store at 4° C., which is stable for one month.

QQ series reagents (not included lipid emulsion, Ca and DMSO) were mixed in a tube, according to the recipe described above. The QQ reagent is then titrated into the protein solution very slowly, drop by drop, while stirring and then add the lipid emulsion. Once the addition of the QQ reagents is completed, the protein solution is left at room temperature for 4 hours before use. During this period, a gently stir is necessary to mix the QQ reagent with protein solution and also to allow the protein modification reaction

TABLE 1

| Recipes | | | | | | | | | | | | |
|---|---|---|---|---|---|---|---|---|---|---|---|---|
| QQ Reagents[a] | 2K | 8K | 12K | 25K | 60K[b] | DOTAP | DOPE | POPC | DMPE | DMSO | MG132 | $Ca^{2+}$ |
| QQ1 | 200 μl | — | — | — | — | 50 μl | 50 μl | — | — | 50 μl | 5 μl | 10 μl |
| QQ2 | 200 μl | — | — | 50 μl | 5 μl | 50 μl | 50 μl | — | — | 50 μl | 5 μl | 10 μl |
| QQ3 | 100 μl | 100 μl | — | 100 μl | — | 50 μl | 50 μl | — | — | 50 μl | 5 μl | 10 μl |
| QQ4 | 100 μl | 50 μl | 50 μl | 50 μl | — | 50 μl | 50 μl | — | — | 50 μl | 5 μl | 10 μl |
| QQ5 | 100 μl | 100 μl | — | 100 μl | — | 50 μl | 50 μl | — | — | 50 μl | 5 μl | 10 μl |
| QQ6 | 100 μl | 50 μl | 50 μl | 50 μl | — | 50 μl | 50 μl | — | — | 50 μl | 5 μl | 10 μl |
| QQ7 | 100 μl | 100 μl | 50 μl | 50 μl | — | 50 μl | 50 μl | — | — | 50 μl | 5 μl | 10 μl |
| QQ8 | 100 μl | 50 μl | 50 μl | 50 μl | — | — | — | 50 μl | 50 μl | 50 μl | 5 μl | 10 μl |
| QQ9 | 100 μl | 50 μl | 50 μl | 50 μl | — | 25 μl | 25 μl | 25 μl | 25 μl | 50 μl | 5 μl | 10 μl |
| QQ10 | 100 μl | 75 μl | 50 μl | 50 μl | — | 25 μl | 25 μl | 25 μl | 25 μl | 50 μl | 5 μl | 10 μl |

[a]Total volume is 5 ml, based on 2-8 mg/ml protein concentration.

[b]2K produces the least cellular toxicity whereas 60K produces the most cellular toxicity to complete. If precipitation is observed, the protein solution can be centrifuged at 14,000 rpm for 15 minutes to remove the precipitate. If the precipitate occurs, a BCA protein assay will be carried out using the supernatant to check the amount of protein remaining in solution. To ensure the efficiency of protein transfer into the cells, the concentration of modified protein has to be high enough at >0.5 mg/ml.

If the majority protein is precipitated, another QQ reagent can be used for protein modification. The QQ series reagents cover a wide range of cationization reagents along with different lipids and enhancers, thus the precipitation problem should be easily solved. The above procedure can be repeated to prepare higher concentrations of modified protein solution for protein transfer into the mammalian cells.

The modified proteins are passed through a desalt column to separate the modified protein from remaining free QQ reagents. The purified protein fractions can be concentrated using a spin column and are stable and can be stored at 4° C. or −20° C. for between a few weeks to a few months.

Different QQ reagents can also be used for the best efficiency of protein transfer as well as the least cell toxicity. In addition, different proteins require modification with different QQ reagent for best efficiency of protein transfer into cells. The following gives several examples:

For in vivo folding experiments of LBD-apoER2, QQ1 was used for the best efficiency of protein transfer into the cells with minimum cellular toxicity.

For in vivo glycosylation experiments of MESD, QQ1 was used for the best efficiency of protein transfer into the cells with minimum cellular toxicity.

For in-cell NMR experiment of apoE, QQ10 was used for the best efficiency of protein transfer into the cells with a minimum cellular toxicity.

Protein Loading into Mammalian Cells.

The fresh modified protein is mixed with cell culture medium (DMEM) with 2% FBS or without, MG132 (3 ng/ml), protease inhibitor cocktail (2 μg/ml), DMSO 30-50 ul/ml and growth factor (1 ng/ml). The newly prepared cell culture medium containing modified proteins is kept in a shake rotator for 10 minutes at room temperature to make sure that the protein is completely dissolved. (For fluorescent imaging experiment, if any precipitation observed at this point, the protein can be centrifuged at 13,000 for 5 minutes to remove the precipitation). The mammalian cells are then added into this culture medium. Before adding the cells into this medium, the cells are seeded for 2-3 days about 70-80% confluent for monolayer cells for fluorescent imaging or 3-5 day old Hela suspending cells. The FBS concentration used in the experiments do not affect the protein delivery.

For protein folding and glycosylation in living cells, both Hela cells and lymphocytes GM001300 cells were used. Before loading modified proteins, the pre-conditioned cells are washed with DMEM medium. The cells are then centrifuged at 1,000 rpm at 25° C. for 20 minutes. The spin-packed cells are resuspended in DMEM cell culture medium and used to load the modified proteins. For loading 4-6 mg bacterial expressed protein, 2.0 ml spin-packed cells were used. The cells are suspended into 2 ml of the DMEM cell culture medium containing modified proteins (2 mg/ml) and then incubated at 37° C. for 2-5 hours.

For in-cell NMR experiments, Hela and lymphocytes GM001300 cells were used. These cells are pre-treated using a medium that contains 10% $D_2O$ overnight. No cell morphology changes were observed after 10% $D_2O$ treatment, suggesting that cells can tolerate 10% $D_2O$ without any obvious cell toxicity. For loading 8 mg bacterial expressed protein, 1-2 ml spin-packed cells were used. The cells are suspended into 2-3 ml of the DMEM cell culture medium containing modified proteins (4.0-8.0 mg/ml) and 10% $D_2O$, and then incubated at 37° C. for 2.5 hours.

Once cell loading of the modified protein is started, the cells are closely monitored using a microscope. Minor cell morphology changes were observed after loading the protein. However, these cell morphology changes are reversible. Upon removing the loading medium and resuspended cell into DMEM culture medium without modified protein for 5-10 minutes, cells are able to return to their original morphology. This minor morphological change of cells after loading with QQ reagent modified proteins depends on the amount of free QQ reagents in the cell culture medium. Initially, a much larger amount of cell morphology changes were detected in free QQ reagents that were not purified from the modified protein. This is because that a large ratio of QQ reagent over protein was used and, after protein modification, a large amount free QQ reagent remained in the cell culture medium and caused cell morphological changes. Once a purification step was added to remove free QQ reagents, only a minor cell morphology change was observed. However, the purification step is generally only necessary when cellular toxicity becomes an issue.

Figure 2A:
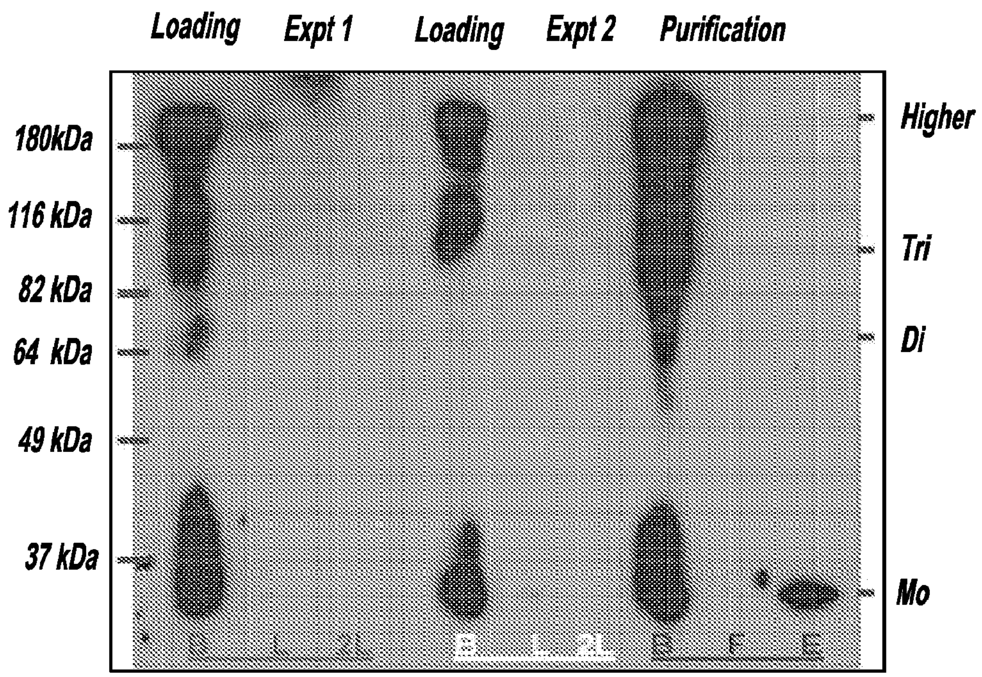
FIGS. 2A and 2B are photographs of western blots using anti-his-tag and anti LBD-apoER2 antibodies, qualitatively showing the efficiency of protein transduction into mammalian cells using the present invention.
Figure 2B:
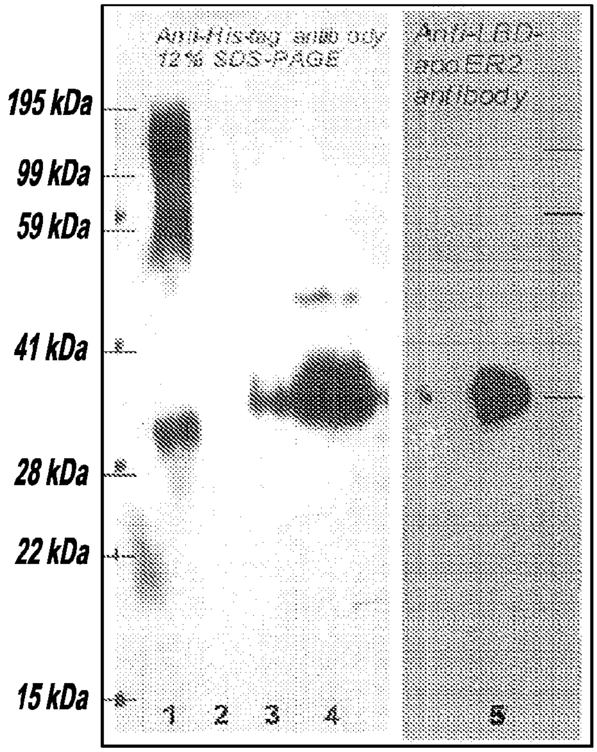
Figure 3:
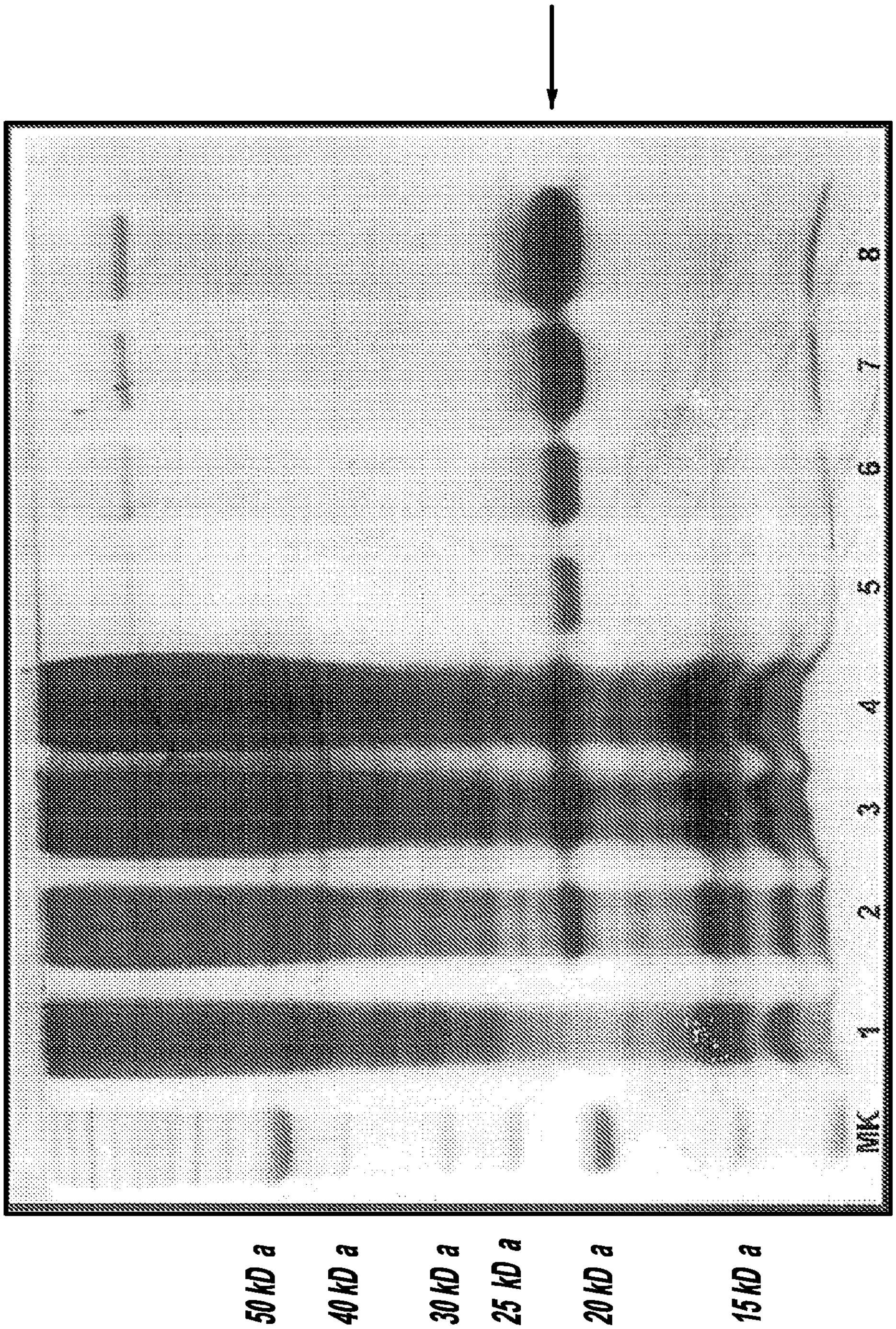
FIG. 3 is a photograph of a SDS-PAGE, quantitatively showing that the present invention can be used to deliver 50-200 μm apoE(1-183) into Hela cells.
Figure 4A:
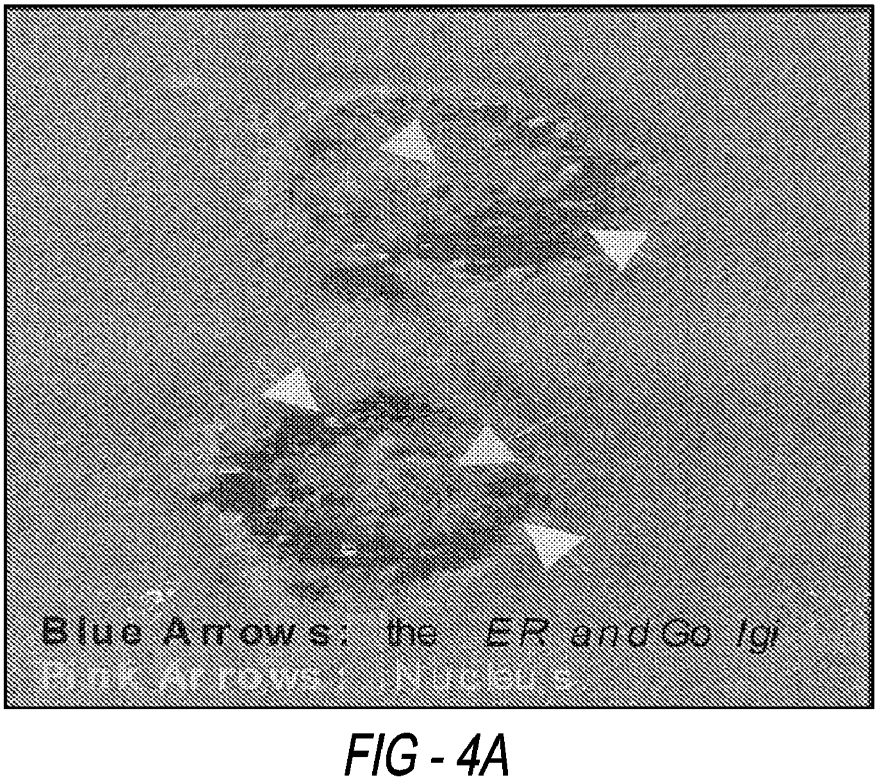
FIGS. 4A and 4B show photographs of fluorescence imaging of Hela cells that were treated with fluorescence labeled, QQ-reagent modified LBD-apoER2 and MESD proteins, showing that the delivered proteins were able to target the ER and the Golgi.
Figure 4B:
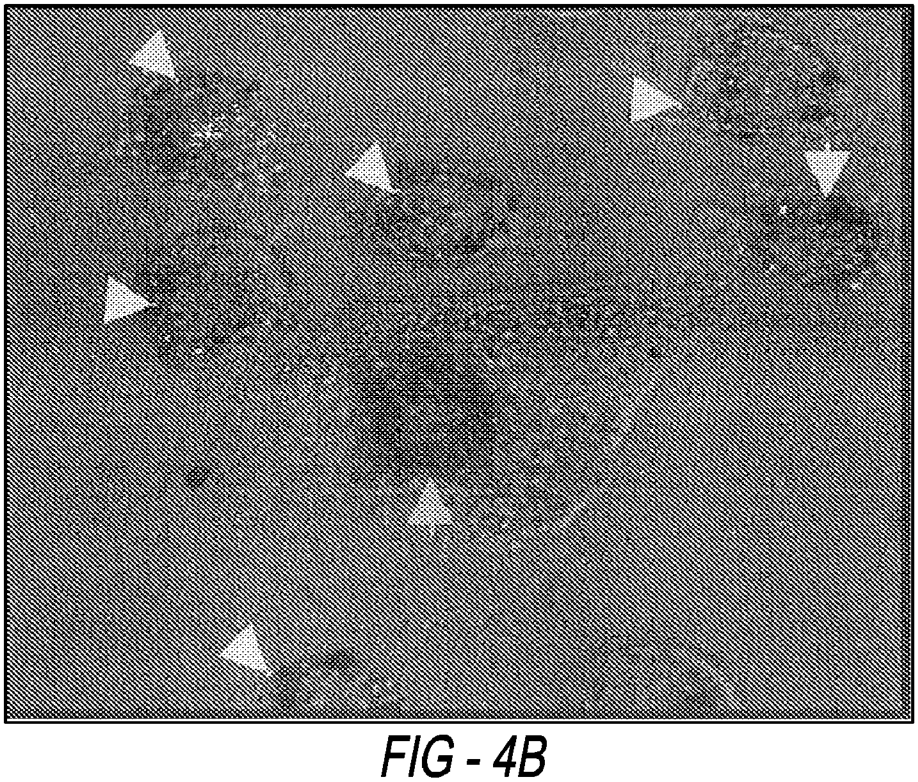

For both in-cell protein folding and glycosylation experiments, a time course study was performed and it was found that the modified proteins were nearly completely transferred into the cells in 3 hours. This is demonstrated by a western blot, showing that no protein remains in the medium after a 2 hour loading (FIGS. 2A and 2B). For in-cell NMR experiments, the modified protein was loaded for 2-3 hours.

After loading the modified protein, the cells are washed with PBS buffer (pH7.4) for 3 times, 15 ml each time. This is a very important step for all experiments. The cells were carefully spun down at 500 rpm for 20 minutes at 25° C., and add 15 ml PBS buffer to wash for 5 minutes with a gentle re-suspension. The cells were again spin down and another 15 ml PBS was added to wash for 5 minutes. The third wash is a wash using a low pH PBS buffer (pH5) to remove any cell surface bound proteins. This wash is only for 1 minute, keeping the cells on ice, and quickly removes the low pH PBS buffer by spin down the cells. The cells were then resuspended into DMEM cell culture medium (pH7.4), which is ready for further experiments.

Protein Folding in the Living Cells:

The Ligand-Binding Domain of apoE receptor 2 (LBD-apoER2) is a 294-residue protein that contains 42 cysteine residues, forming 21 intra-molecular disulfide bonds. A proper folding of this protein is extremely difficult since it can form both intra- and intermolecular disulfide bonds. Bacterial expression of this protein can't produce a properly folded LBD-apoER2. In the mammalian cells, apoER2 is properly folded in the ER, with the help of folding enzymes and chaperones. In particular, there are two specialized chaperone proteins, RAP and MESD, specifically promoting the correct fold of the LDLR superfamily (1-2). RAP (Receptor Associated Protein) is a 323-residue ER-resident protein that specifically promotes the LBD fold, and escorts the mature, properly folded protein trafficking from the ER to the Golgi (3-4). In contrast, MESD (Mesoderm development) is a 195-residue ER-resident protein that contains an ER retention signal in its C-terminal domain (5-6). The biological function of MESD is to promote a proper folding of the YWTD/EGF domain of the LDLR superfamily (5-7).

LBD-apoER2 was used as a model protein for this experiment, simply because it is very difficult to correctly refold in vitro due to its rich in cysteines. The present invention utilizes the folding machinery of the mammalian cells to help LBD-apoER2 proper folding. Based on this, the present invention provides transferring bacterial expressed LBD-apoER2, which is not folded properly and non-functional in terms of ligand-binding, into the mammalian cells. After being transferred into the cells, the misfolded LBD-apoER2 has an ability of entering cell apparatus, such as ER, and therefore can be properly folded in the ER, similar to the endogenous apoER2. This is supported by several previous publications, indicating that the transferred exogenous proteins are able to reach inside of nucleus of the mammalian cells (7-8). The folding machinery in the ER of the mammalian cells makes the bacterial expressed protein fold properly.

LBD-apoER2 is expressed in bacteria as a His-tag fusion protein. Bacterial expression was optimized and is able to produce 300 mg LBD-apoER2 from one-liter cell culture. Using SDS-PAGE, it was shown that the bacterial expressed LBD-apoER2 is mis-folded and form different oligomers due to inter-molecular disulfide bond formation. Using a ligand blot (far western), it was demonstrated that the bacterial expressed LBD-apoER2 is incapable of binding to its ligand, such as RAP and apoE.

QQ series reagents were used to modify LBD-apoER2. In this case, QQ1 is used to modified LBD-apoER2, following the protocol describe above. After modification, LBD-apoER2 (1.0 mg/ml) is incubated with Hela cells at 37° C. for 2 hours to allow cells to load the modified LBD-apoER2. The cells were gently spun down and a western blot of the medium was run using an anti-his-tag antibody to check the loading efficiency. In most cases, the cells loaded most of the modified LBD-apoER2, and western blot of the medium either show no band or a very weak band of LBD-apoER2. The cell pellet is resuspended into DMEM cell culture medium and incubated for a period that allows the misfolded LBD-apoER2 to fold into its native conformation in living cells.

The incubation is stopped by spin-down of the cells, which are then washed. The cell pellet is lysed using a sonication method with addition of protease inhibitor. The sonication uses a power of 7-8 on a sonicator from Fisher Scientific (Sonic Dismembrator, Model 100) with a micro probe. Each sonication lasts 1 minute on ice and is repeated three times. There is a 3 minutes interval between sonications to prevent over heating. The supernatant fractions are combined. The pellet is dissolved into a buffer that contains 1% SDS. Both supernatant and pellet fractions are used for ligand blots (far western blots) or pull-down experiments using RAP and apoE as the ligand, to probe the folding and function of LBD-apoER2

Two assays are used to probe the proper folding and functions of the in cell refolded LBD-apoER2. One is a ligand-blotting assay and the other is a pull-down assay. The details of these two assays are described in the following:

Ligand Blot:

Cell lysate (supernatant or pellet fraction) is loaded onto either a non-reducing SDS-PAGE (For RAP) or a native gel (apoE/DMPC). The gel is run in a cold room. The protein is then transferred onto a nitrocellulose membrane at 380 mA for 2 hours. After transfer, the membrane was incubated at room temperature with either RAP (40 μg/ml in 2% dry milk PBS) for 2 hours or incubated with apoE/POPC complex (50 μg/ml in 2% dry milk PBS) for 2 hours. The membrane is then washed three times with 20 ml/each PBS for 5 minutes each time, to remove unbound RAP or apoE/POPC. The membrane is incubated with anti-RAP mAb or anti-apoE poly Ab for 1 hour in 2% dry milk PBS, followed by incubation with HPR-conjugated secondary Ab for 1 hour. Finally, the membrane is detected using ECL (Pierce). Using this assay, a band is observed at the molecular weight of LBD-apoER2 (34 kDa) for the complex of ligand/LBD-apoER2.

Pull-Down:

Cell lysate (supernatant or pellet fraction) is in the binding buffer (2 mM imidazole) for the His-tag beads and loaded onto the beads. Since the LBD-apoER2 contains a his-tag, this protein binds to the his-tag beads, whereas all other proteins in the cells do not bind to the beads and can be washed out with binding buffer. After loading, the beads (~0.2 ml) is washed with 5×5 ml washing buffer, containing 10 mM imidazole, to remove the unbound proteins from the His-tag beads. The purified beads are then incubated for 1 hour with either RAP or apoE/POPC particles that are prepared previously using the cholate dialysis method. This step allows the refolded LBD-apoER2 to bind to either RAP or apoE/POPC. The beads are then washed with 5×5 ml PBS buffer, pH7.4, to remove the unbound ligand. The ligand/LBD-apoER2 complex is eluted out using an elution buffer containing 0.2 M immidizole. An aliquot of the eluted ligand/LBD-apoER2 was mixed with 2% SDS loading buffer (for SDS-PAGE only) and loaded on a SDS-PAGE or native gel, and is subjected to western blots using the anti-ligand antibodies. Using this assay, a band should be observed at the ligand molecular weight (SDS-PAGE) or ligand and LBD-apoER2 complex (Native Gel), if LBD-apoER2 is functional and binds to the ligands. For example, in RAP/LBD-apoER2 pull-down experiment should show a band at 73 kDa.

For both ligand blotting and pull-down experiments, several controls are included:

1. Hela cell lysate only (without loading the modified protein, to test endogenous protein).
2. Bacterial expressed LBD-apoER2 that is not properly folded (serve as a negative control).
3. ApoE/POPC particles (Serve as a control).
4. Cell lysate from unload protein cells as column wash control.

In a pull-down experiment, all of the control groups were negative.

Protein Post-Translational Modifications in Living Cells:

Another question is whether the transferred exogenous proteins undergo post-translational modifications inside of the cells. These exogenous proteins may undergo post-translational modifications inside the cells if they are able to get into the ER and Golgi. Our data indicated that the transferred exogenous protein, LBD-apoER2, is able to get into the ER for its proper folding.

Protein glycosylation is the important step in studying protein post-translational modifications. First, it must be confirmed whether the transferred exogenous proteins undergo glycosylation. Once this is proven, testing on phosphorylation and ubiquitination of the transferred exogenous proteins can occur.

MESD, a known glyco-protein, have been transferred into the cells. The cells were lysised and the proteins were probed using western blots. Higher molecular weight bands were observed for MESD than the band of bacterial expressed MESD as controls. In addition, the molecular weight of MESD band increases along with the length of incubation of the cells after protein transformation. For example, a one-hour incubation after transformation resulted in a two bands at molecular weight of 25 and 35 kDa (MESD is a 25 kDa protein). A five hour incubation generated an additional band at ~45 kDa for MESD. The experiment was repeated several times and the same phenomena were always observed. The increase in molecular weight of MESD is due to glycosylation, since deglycosylation enzymes converted the two higher molecular weight bands (35 and 45 kDa) into one single band at 25 kDa that is the same as the bacterial expressed MESD.

Experimental Details:

0.5 mg of modified MESD is incubated with Hela or GM001300 cells at 37° C. for 1-5 hours. The cell culture medium (5 ml) contains 5% FBS, 1 ng/ml of MG 132 and 2 μg/ml protease inhibitor cocktail. After incubation, cells were washed with 3×15 ml PBS. Each wash includes adding 15 ml PBS into the cell pellets and re-suspension, following by spin-down the cells at 500 rpm for 20 minutes at 25° C. The cells are lysed using sonication and spun down at 6000 rpm for 5 minutes. The pellet is dissolved using a SDS loading buffer (2% SDS) and heat at 80° C. for 15 minutes with DTT. Both the supernatant and pellet fractions are probed with a western blot using a polyclonal antibody against MESD. At 1 hour cell loading, the western blots of both supernatant and pellet fractions show mainly a band at a molecular weight of 25 kDa, which is identical to the band of bacterial expressed MESD, with a minor band at 35 kDa. However, at 5 hour cell loading, an additional band at 45 kDa was observed.

Enzymatic de-glycosylation reaction of the products was carried out using neuraminidase and PNGase. Time courses of both enzymatic reactions finally converts both the 35 and 45 kDa bands to the 25 kDa band which is identical to the band of the bacterial expressed MESD. Thus, this result confirms that MESD is glycosylated inside the cells. MESD contains an ER retention signal in its C-terminal domain. Once this protein gets inside the ER, it may stay inside the ER, therefore, is subjected to post-translational modification, including glycosylation.

Exogenous MESD Follows the Same Secretion Pathway as Endogenous MESD Inside Hela Cells Since MESD is glycosylated inside Hela cells, it suggests that the transduced MESD travels to the ER and Golgi, the two cell compartments where post-translational modifications occur. To confirm this, an experiment was performed to identify the intracellular location of MESD after transduction. First, MESD was labeled with green-ArrayIt and then purified from free green-Arraylt using a desalt column. Fluorescence labeled MESD was then modified with QQ1. The modified, fluorescence labeled MESD was incubated with Hela cells for 3 hours and then the cells were taken for fluorescence imaging using a ApoTom (Zeiss) Ax10plan 2 Imaging system.

Figure 5A:
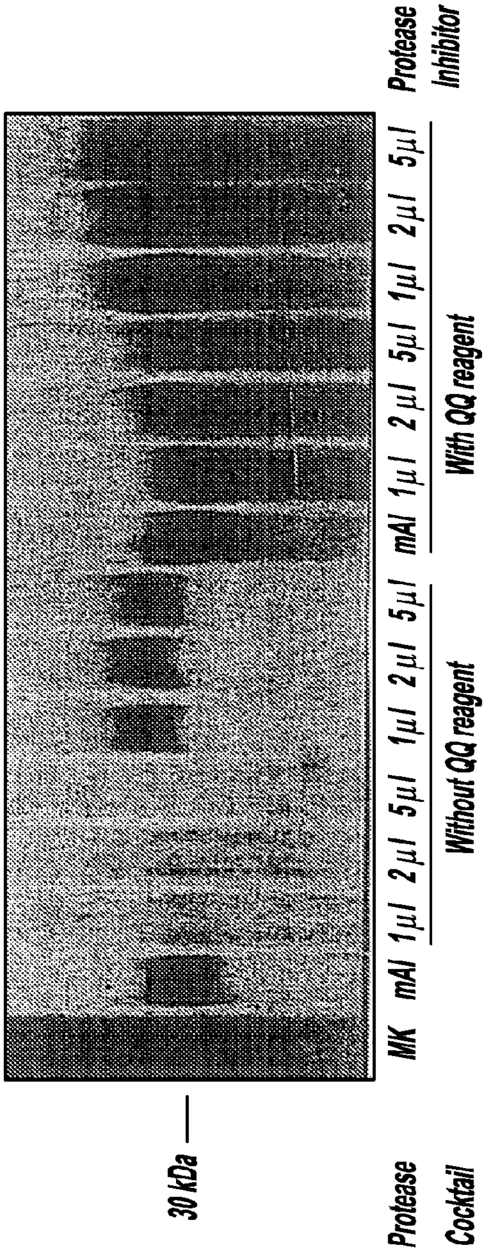
FIGS. 5A and 5B show photographs of SDS-PAGEs, suggesting that the QQ reagent modified mouse apoAI was protected from degradation by proteases, both protease cocktail and cellular proteases.
Figure 5B:
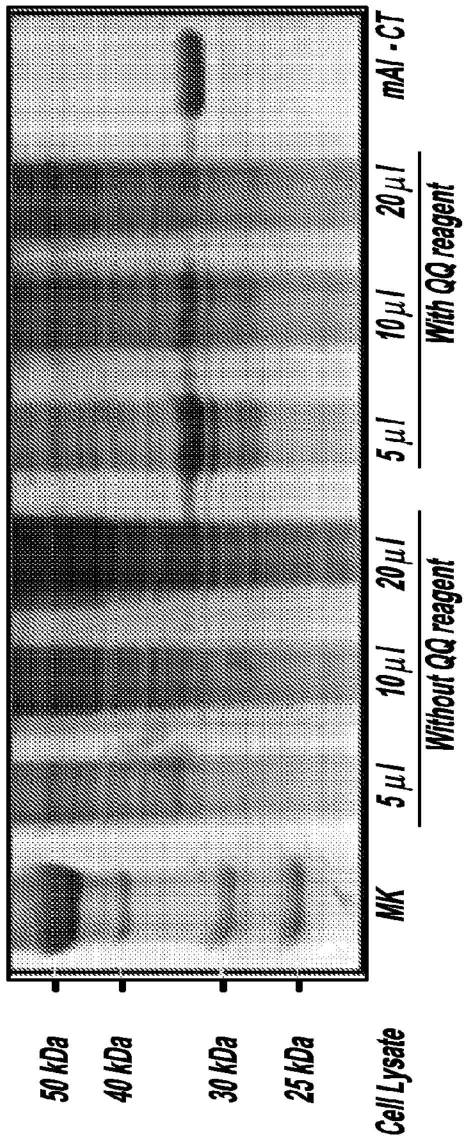
Figure 5C:
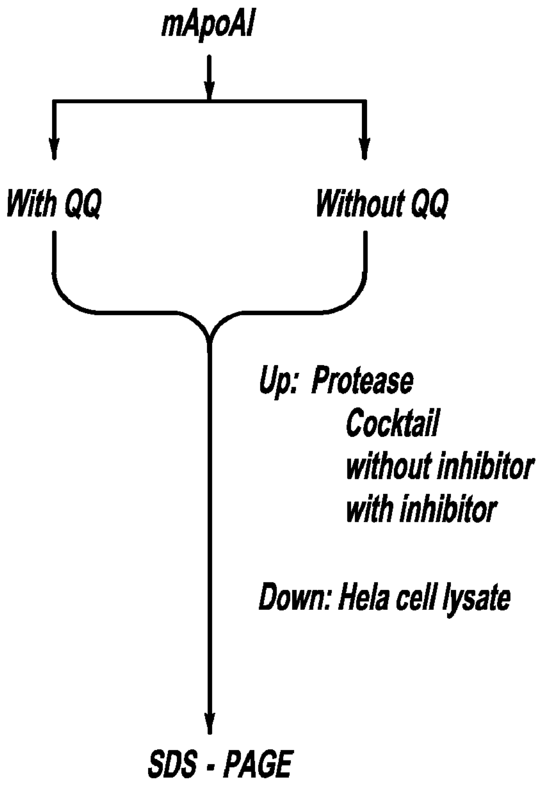
FIG. 5C is a diagram of an experimental procedure.
Figure 6A:
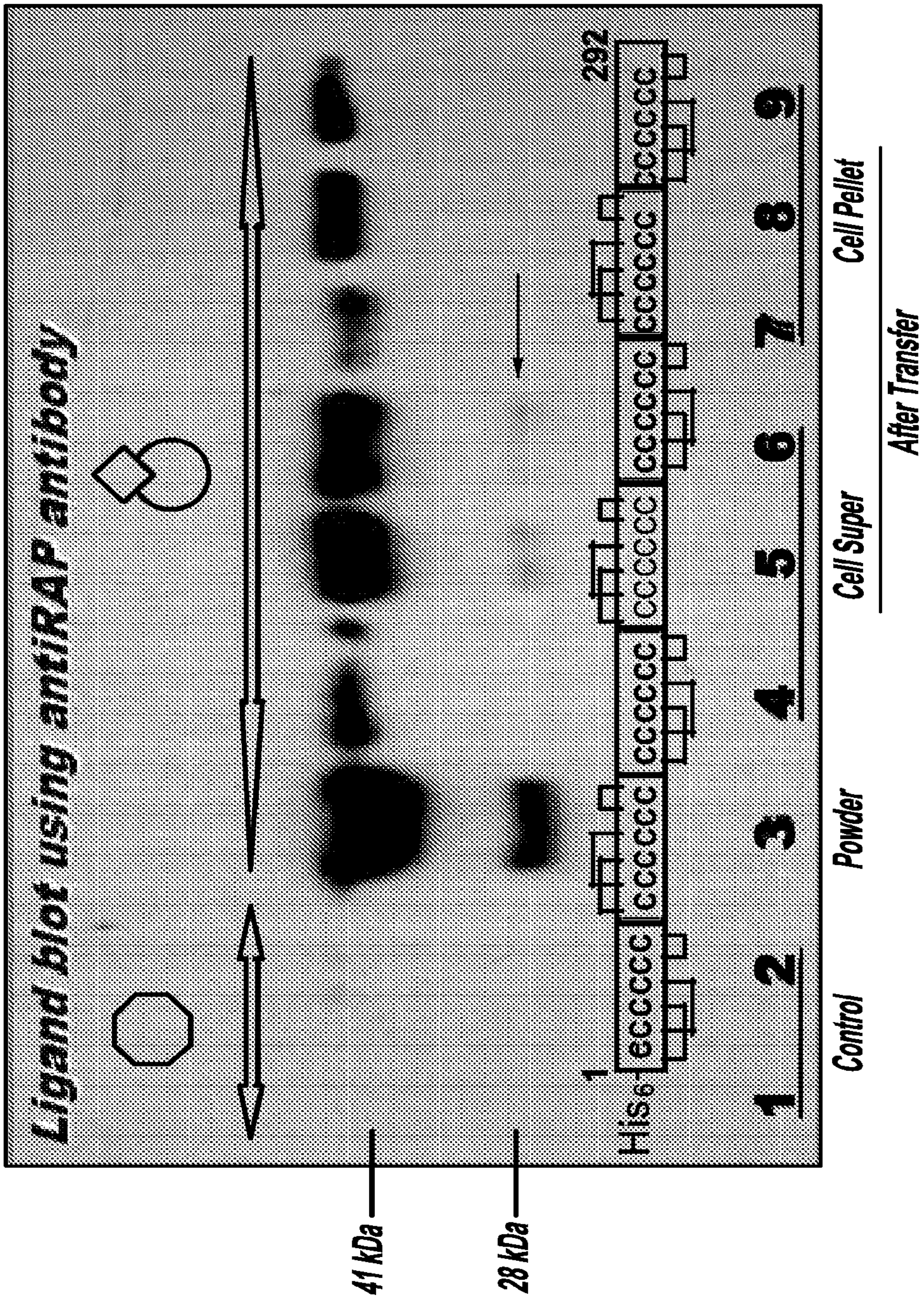
FIGS. 6A and 6B are photographs of far western blot of LBD-apoER2 using anti-RAP (FIG. 6A) and anti-apoE (FIG. 6B) antibodies, showing that the transduced LBD-apoER2 was properly folded and functional for binding to both. RAP and apoE.
Figure 6B:
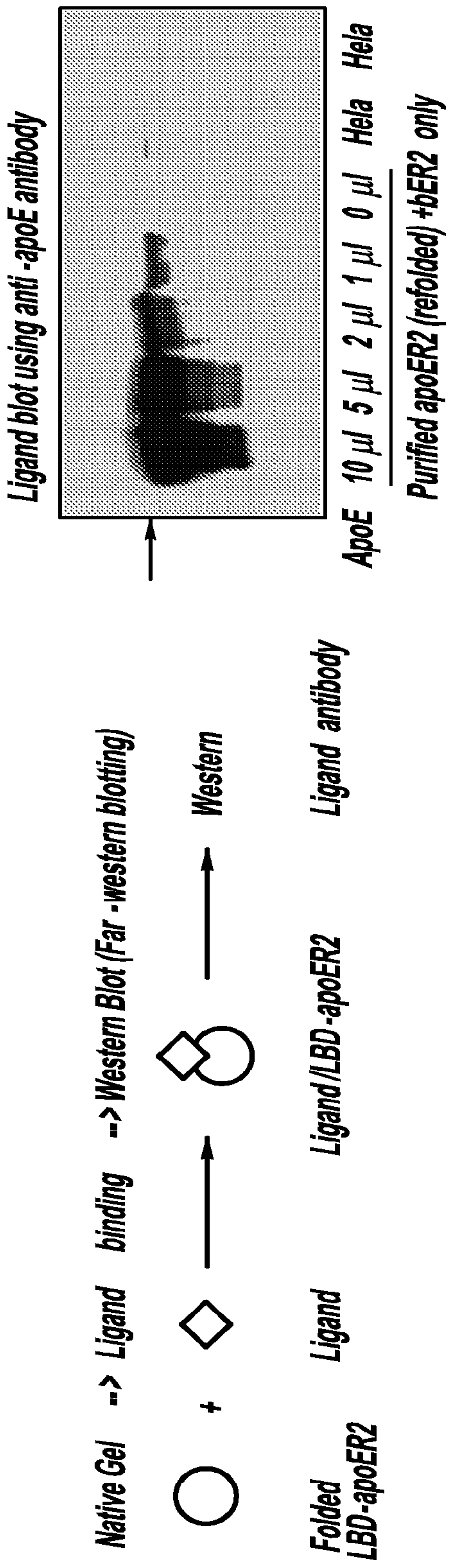
Figure 7A:
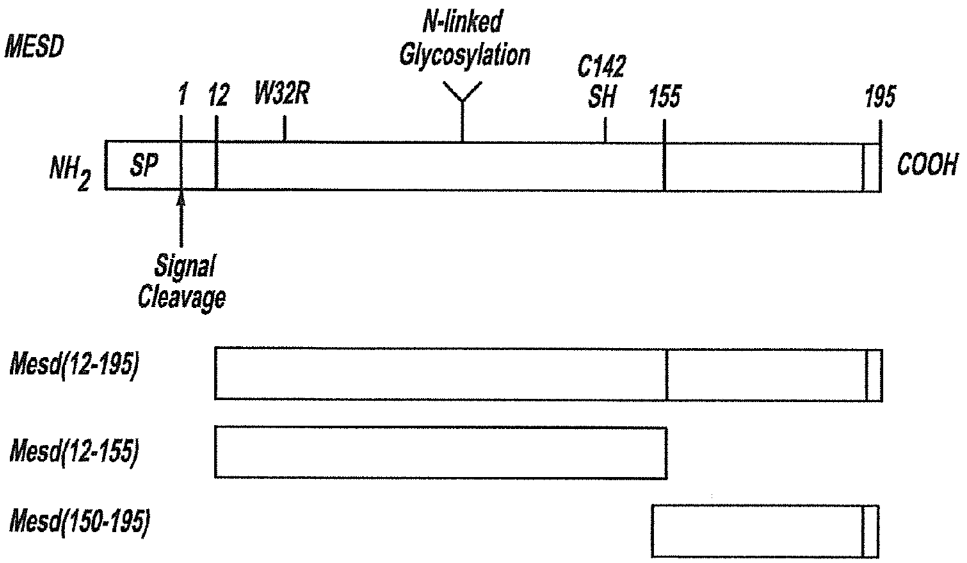
FIG. 7A shows diagrams of MESD proteins.
Figure 7B:
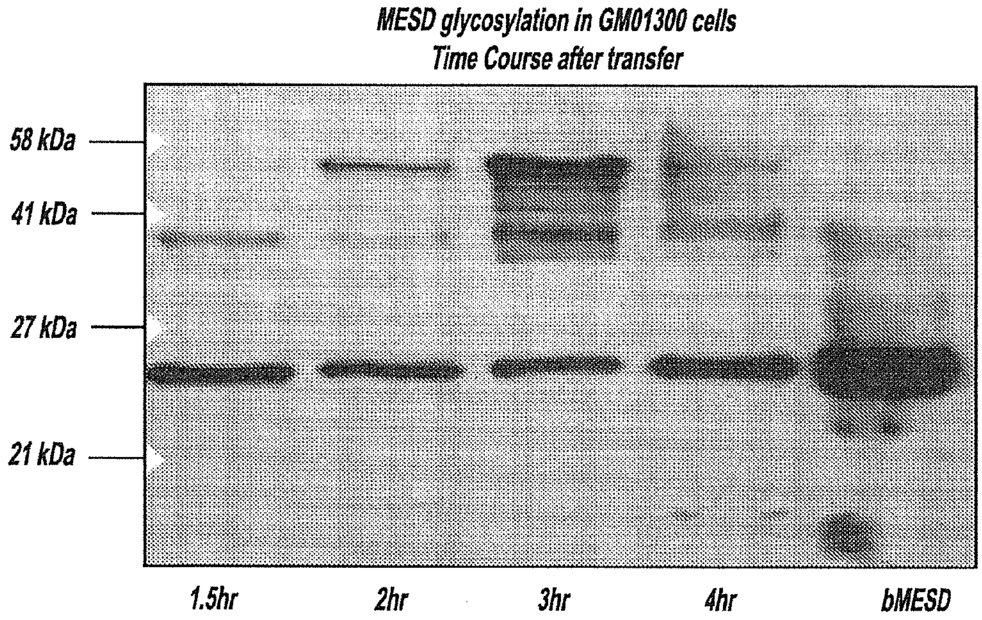
FIGS. 7B, 7C and 7D are photographs of western blots of the exogenous MESD proteins that were delivered into GM01300 cells (FIG. 7B) and the endogenous MESD from eight different mammalian cell lines (FIG. 7C), showing the same three band pattern. In contrast, MESD(12-155), which lacks the "REDL" ER retention signal, only shows one single band that is the same as the bacterial expressed MESD(12-155) (FIG. 7D).
Figure 7C:
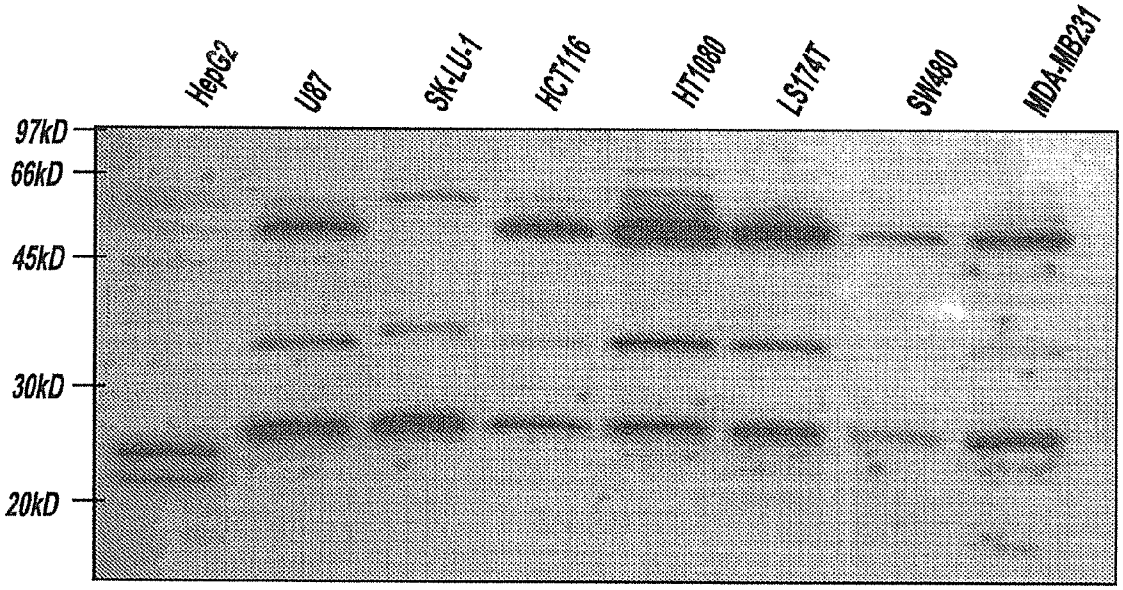
Figure 7D:
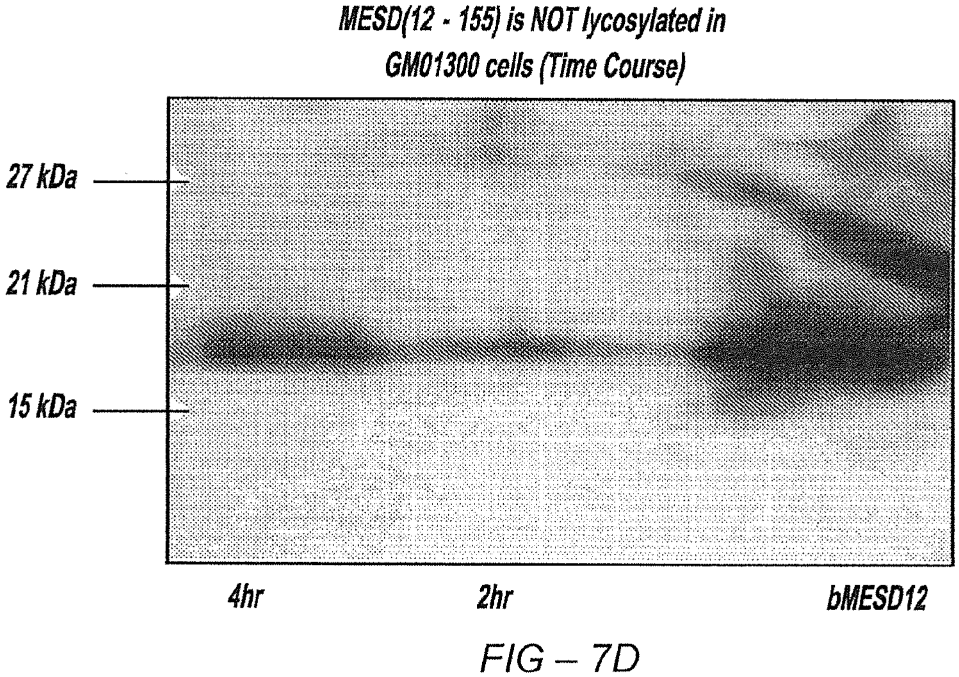
Figure 8A:
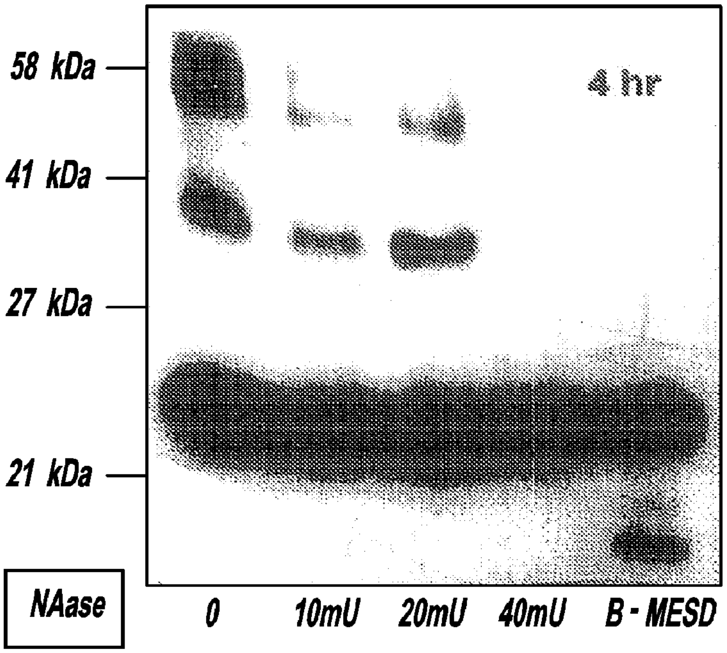
FIGS. 8A and 8B are photographs of western blots of the MESD in the Hela cells that was treated with two different de-glycosylation enzymes: PNGase (FIG. 8A) and NAase (FIG. 8B), confirming that the upper bands were glycosylated forms of MESD.
Figure 8B:
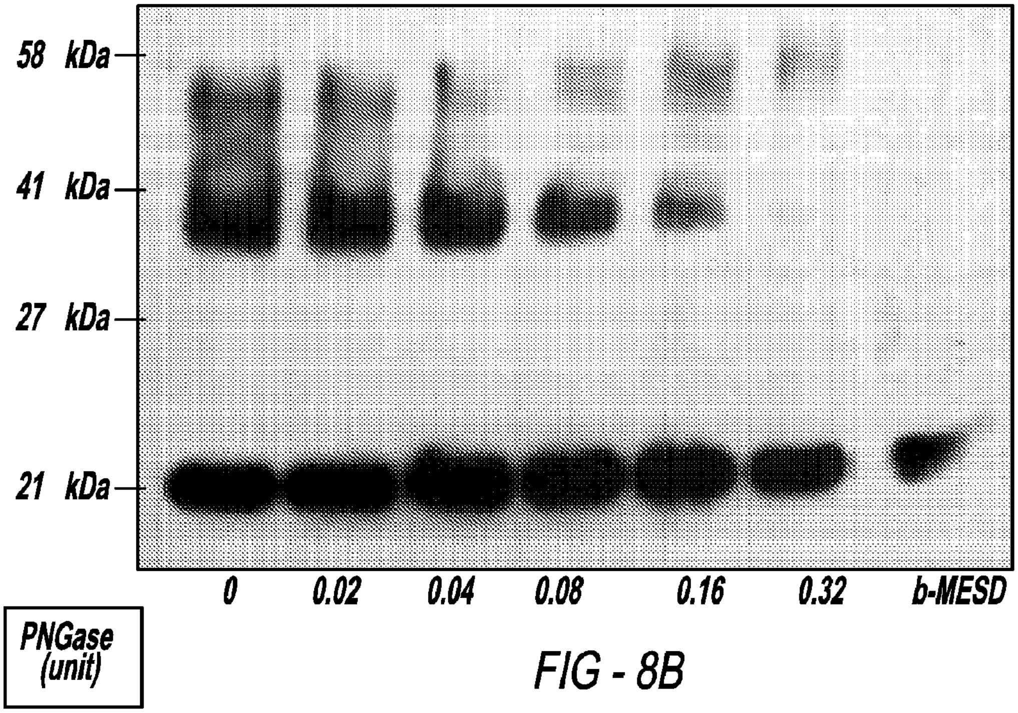
Figure 9A:
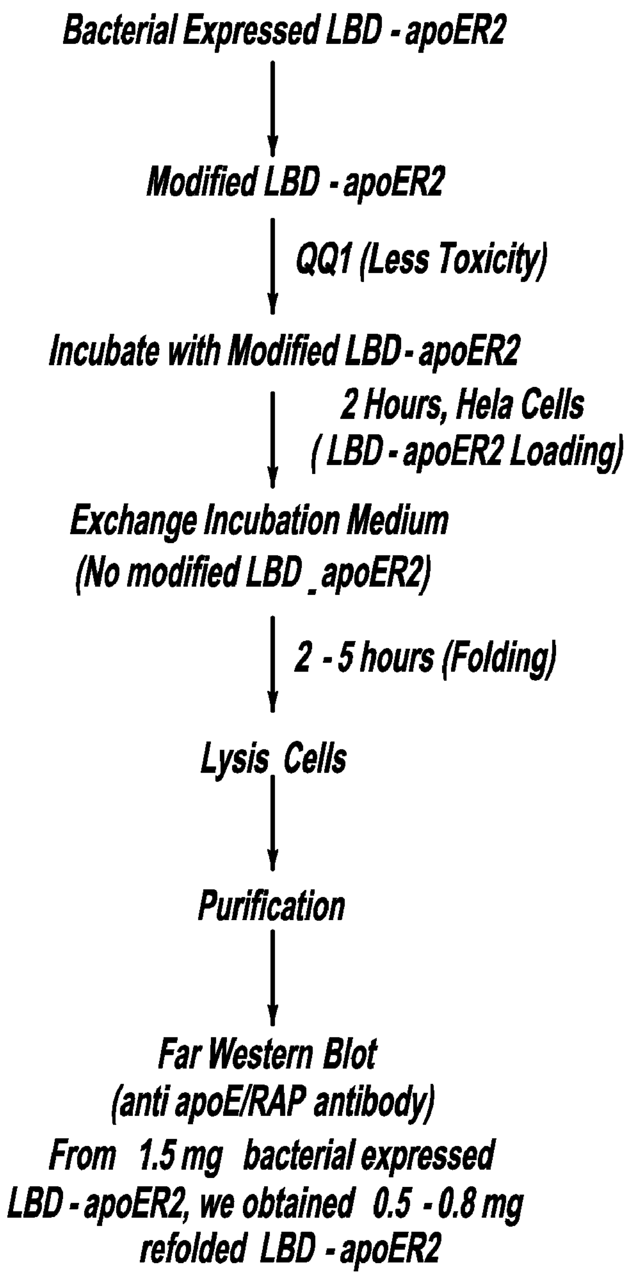
FIG. 9A shows the flow chart of purification of LBD-apoER2.
Figure 9B:
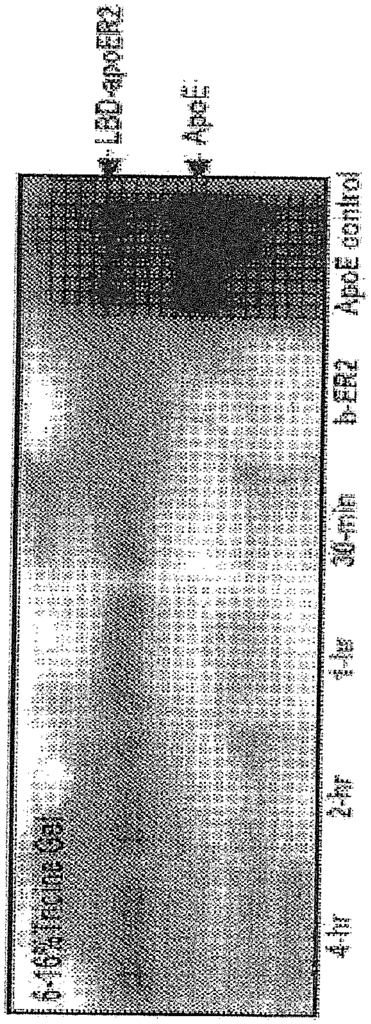
FIGS. 9B-9D are photographs of far-western blots of purified LBD-apoER2 from Hela cells using a His-Bind resin column, showing that purified LBD-apoER2 binds to ApoE and RAP.
Figure 9C:
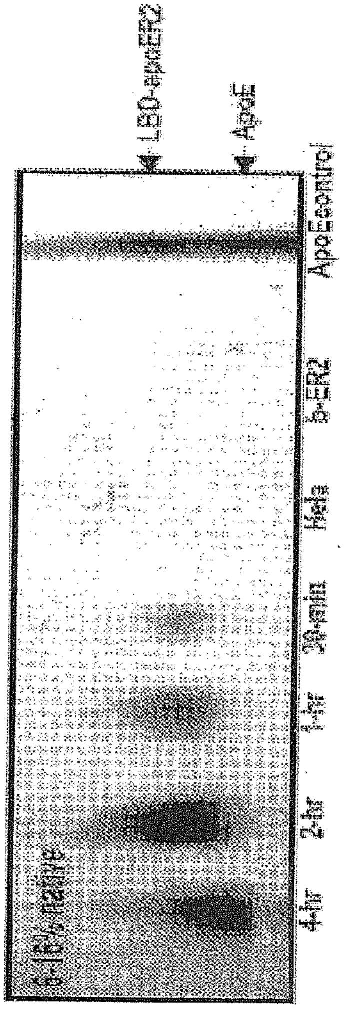
Figure 9D:
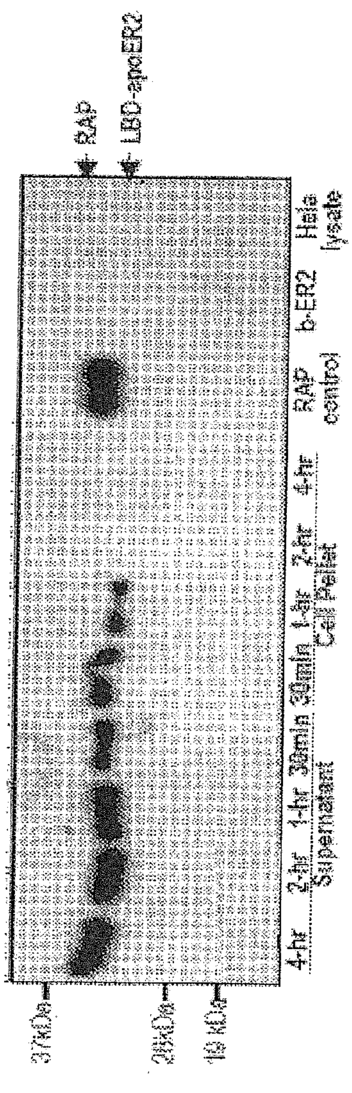

The fluorescence imaging clearly showed that the MESD was primarily located in the peri-nuclei areas that are either the ER or the Golgi. This data confirmed that the exogenous MESD traveled to the ER and the Golgi where the folding and post-translational modification occurred. It seemed that the QQ reagent could target MESD into the ER and the Golgi. In addition, the data further suggested that the exogenous MESD stayed in the ER and the Golgi. To further identify what caused MESD to travel to and stay in the ER and the Golgi, a MESD construct, MESD(12-155), was prepared that removed the ER retention signal. The data indicated that no glycosylation was observed in this case (FIGS. 5A-5B). Therefore, the data indicated that it was the REDL ER retention signal of MESD that directed the exogenous MESD to travel to and stay in the ER and the Golgi after transduction inside the cells. Thus, the exogenous MESD follows the same secretion pathway as the endogenous MESD.

It is a very important conclusion, since this conclusion indicates that the exogenous proteins follow the Blobel's "Signal Theory", suggesting that the signal sequences of proteins direct the fate of all proteins, regardless their endogenous or exogenous origins, once they are inside the cell. This conclusion further indicates that the exogenous proteins follow the same secretion pathway as that of endogenous proteins, providing the physiological and pathological relevance of the applications of protein transduction technology.

Experimental Details:

2 mg MESD in 200 μl PBS buffer, pH 7.4 (10 mg/ml), was dissolved overnight. The solution was spun for 10 minutes at 12,000 rpm at room temperature. 70 μl protein solution was taken and 0.5 μl of green-Arraylt was added at room temperature. An incubation was carried out for 6 hrs to overnight in cold room and then purified using a desalt spin-column at 10,000 rpm for 2 minutes to remove free dye. The purified, fluorescence labeled protein was modified by QQ1, as described, using 10 μl of QQ1 stock solution, and incubated overnight without further purification.

Hela cells were seeded three days before the experiment. Hela cells were incubated with QQ1 modified, fluorescence labeled MESD in DMEM culture medium for 1-3 hours in 37° C. The cells were very healthy after the incubation, displaying normal morphology. The cells were washed with PBS seven times to remove any MESD in the medium. Hela cells were then used for fluorescence imaging using an ApoTom (Zeiss) Ax10plan 2 Imaging system. The fluorescence imaging experiments were carried out at 486 nm with dipping lens in the PBS with anti-fading reagents and protease inhibitor to observe live cells. Photos were taken under light and fluorescent overlayers to view the cell body and fluorescence labeled MESD.

High-Level Production of the Properly Folded, Functional Protein Using in-Cell Folding Technology Using an in-cell folding technology, it was demonstrated that mammalian cell folding machinery could be used to properly fold LBD-apoER2, which was impossible to fold in bacteria (Section VII). The next goal was to purify this properly folded, function LBD-apoER2 for structural and functional studies. This technology can be used to produce large quantities of properly folded, functional LBD-apoER2. Since the bacterial expression system produces 300 mg/liter purified. LBD-apoER2, the technology can produce hundred mg quantity of the properly folded, functional LBD-apoER2. This is a major advance in production of functional proteins, which is extremely important for pharmaceutical industry, since the technology can produce hundred milligrams of therapeutic protein for disease treatment purpose.

Since a his-tag was introduced in the N-terminal domain of LBD-apoER2, protein purification of in-cell folded LBD-apoER2 was carried out used a his-tag binding resin column. The results indicated that from 1.5 mg bacterial expressed LBD-apoER2, 0.5-0.75 mg properly folded, functional LBD-apoER2 can be obtained. This purification was repeated several times and obtained a similar yield. It was also demonstrated that the purified protein is properly folded and biologically functional and is able to bind to both RAP and apoE/POPC particles.

Experimental Details:

The first part (Protein loading and in-cell folding) is essentially the same as above. The only difference is the incubation time after protein loading into the cells. The cells were loaded with modified LBD-apoER2 for 3 hours. After loading, the cells were incubated in the DMEM cell culture medium, containing 5% FBS, MG132 (3 ng/ml), protease inhibitor cocktail (2 μg/ml), for 2-5 hour before spin-down, to ensure that most transferred LBD-apoER2 is correctly folded.

After incubation, cells were washed using PBS three times, 15 ml each time. After wash, the cells were spun-down gently at 2000 rpm for 5 minutes. The cell pellet (0.5 ml) was resuspended in 2 ml cell lysis buffer, which is a PBS buffer, containing 2% Triton-X, 2 μM PMSF, 2 μg/ml protease inhibitor and 2 ng/ml MG132, pH 7.4. The cell suspension was incubated on ice for 30 minutes and sonicated for 30 seconds at a sonication power at 4 using a sonicator from Fisher Scientific (Sonic Dismembrator, Model 100) with micro probe. Cell lysate was spun down. The cell pellet was dissolved again using cell lysis buffer and sonicated again for 30 seconds. The supernatant fractions were combined and loaded on a small his-tag binding column (0.3-0.5 ml). The column was washed using 50 ml PBS buffer first and then washed again with 25 ml PBS buffer containing 2 mM imidazole. A 20 μl of his-tag beads were taken out and dissolved into 20 μl of SDS loading buffer. This sample was loaded onto a SDS-PAGE to check the protein purity. If the protein is not pure, more washing buffer would be used. This purification was carried on in the cold room. All buffers, including loading buffer and washing buffer, contain 2 μM PMSF and 1 ng/ml MG132. Protein was eluted with 1 ml elution buffer that contains 300 mM imidazole, 50 mM phosphate buffer, containing 50 mM NaCl, 2 μM PMSF and 1 ng/ml MG132.

The eluted protein was dialyzed overnight against 150 ml PBS buffer at 4° C. using a small dialysis cassette (Maximum volume: 3 ml). The PBS buffer was changed twice during dialysis to ensure the removal of imidazole. After dialysis, the properly folded LBD-apoER2 was taken out of the dialysis cassette, add MG132 at 1 ng/ml and store at −80° C. freezer. For long-term storage, the protein sample was freeze-dried into powder.

The purified LBD-apoER2 was probed for its folding and function. Two functional assays: Ligand blot and pull down experiments were performed to probe the function of LBD-apoER2. In addition, both RAP and apoE/POPC were used as the ligand for LBD-apoER2. Both assays demonstrated that the purified LBD-apoER2 is functional and capable to bind to both RAP and apoE/POPC, whereas the bacterial expressed LBD-apoER2 was not functional.

In addition to LBD-apoER2, the present invention enables one to prepare properly folded YWTD/EGF domain of apoER2. For this purpose, the first YWTD/EGF domain and the first two YWTD/EGF domains of LRP6 were bacterially expressed. LRP6 is an important cancer suppressor that contains four YWTD/EGF domains before the three LBD repeats and transmembrane and cytoplasmic domains. This receptor is coupled with the wnt signaling, serving as a co-receptor for wnt, which is critical to many human diseases, including cancer and Alzheimer's disease. LRP6 and apoER2 have a complete different modular structure arrangement for the LBD and YWTD/EGF domains. In addition, production of the following functional proteins are currently carried out: LCAT, CETP, PLTP and several membrane proteins, such as ABC-G1, ABC-G4, and SR-BI. These proteins are important proteins that are involved in reverse cholesterol transport pathway and responsible for enhancement of the HDL (Good cholesterol) level in plasma. In addition, mouse PMP22 has also been expressed using *E. coli*. PMP22 is a membrane protein that contains putative four transmembrane domains. The preliminary data indicates that bacterial expression of these proteins produces an incorrect folding, thus are not functional.

In-Cell Nuclear Magnetic Resonances (NMR) Technique

Current high-resolution structural biology techniques, including X-ray crystallography and NMR, allow for structural determination of protein, DNA and RNA at an atomic resolution. However, these techniques only determine the structures of macromolecules in the test tube. There is no high-resolution structural biology techniques permits to solve structures of these macromolecules in the living cells.

Several studies, using NMR, investigate protein structures in the living cells, primarily focusing on bacterial cells and oocytes (1-4). For NMR studies, a protein has to be isotropically labeled with stable isotopes, such as $^{15}N$ and $^{13}C$. For large proteins (MW>25 kDa), protein has to be triple-labeled with $^{2}H$, $^{15}N$ and $^{13}C$. For bacterial cells, a protein can be high-level expressed in minimum medium ($HN_4Cl$, nitrogen source, glucose: carbon source) and isotope labeling can be readily performed with a low cost (using $^{15}NH_4Cl$ as nitrogen source, $^{13}C$-glucose as carbon source and $D_2O$). However, this isotope labeling strategy for bacterial expression not only labels the protein of interest, but also labels all the other bacterial proteins. Since the protein of interest is high-level expressed at >10-100 folds higher than bacterial proteins, the NMR signals are mainly come from the protein of interest. Nevertheless, bacterial proteins will give rise to a high background signals in the NMR spectra. In contrast, oocytes are large cells and can be used to micro-inject a large amount of isotope labeled protein into the cells. Thus NMR data of the oocytes can be collected. These studies utilized techniques that can only apply to bacterial cells and oocytes. Currently, there is no technique that permits to study protein structure at atomic resolution in the mammalian cells.

Using the present technique, isotropically labeled proteins can be produced using bacteria. The isotropically labeled proteins are modified using QQ reagents and then incubated with the living mammalian cells. The modified, isotropically labeled proteins can be transferred into these mammalian cells, which allow collection of 1D/2D/3D-NMR data for structural determination purpose. In order to collect 2D/3D NMR data for structural determination of a protein in the living cells, several major problems have to be solved:

1. Higher protein concentrations in living cells. NMR technique is not a sensitive technique that requires a high sample concentration for detection for 2D/3D NMR experiments. With a cold probe of 600 MHz NMR instrument, a sample of 50-200 μM is required for a 1-2 hour experiment for a regular 2D HSQC experiment. In contrast, for a 3D NMR experiment, a sample of 300-500 μM is required for a 2-3 day experiment.
2. Cell survival for at least for 3 days as a cell slurry state in the NMR tube. Since a 3D-NMR experiment requires 2-3 days data collection time, the cells have to be survival for at least 3-days as a slurry state in the NMR tube.
3. Cells have to be trained in a cell culture medium with 5-10% $D_2O$. Since NMR experiment requires 5-10% $D_2O$ to lock the magnetic field, the cells have to be able to survive in a culture medium that contains 5-10% $D_2O$.
4. Subcellular protein locations. To ensure physiological and pathological relevance of in-cell NMR, the transduced protein has to be targeted to the correct cell compartments where the biochemical reaction occurs for this protein.

Experimental Details:

Proteins were modified based on the method described above with QQ9 or QQ10. For each in-cell NMR experiment, 4-10 mg of protein was modified freshly each time. If there is any precipitate after protein modification, the modified protein solution was spun down and supernatant was used for further experiments. The QQ reagent modified protein was purified from free QQ reagents using a desalt spin column. The purified protein was concentrated to have a high concentration that ensure >1-2 mg/ml after mixing with the cell loading medium that contains: 0.5% FBS, 10% $D_2O$, MG132 1 μM and protease inhibitor 2 μM.

The cells (Hela or GM001300) were pre-incubated with 10% $D_2O$ in the DMEM cell culture medium with 10% FBS for 24 hours. The cells were then mixed with the cell-loading medium. After mixing with the loading medium, the cells were closely monitored every ten minutes using a microscope. Several different QQ reagents were tested and it was found that different QQ reagents produced different cell toxicity. The general strategy is to choose a QQ reagent that gives a good cell loading efficiency of the modified protein while produces the least cell toxicity. This is because the cell preferably survives for more than three days in the NMR tube for NMR data collection. QQ6-QQ10 reagents generally serve for this purpose.

Protein was loaded into cells for about 2-3 hours at 37° C., on a rotator depending on cell morphology changes. If there was no or a minimum cell morphology change, cells could be loaded for a longer time, such as 2-4 hours, so that more protein could get into the cells. In contrast, if there was a significant cellular morphology change or cells started to lysis, the loading was stopped. Cells were scraped from flasks and cell number in the suspension was adjusted into $1\times10^9$/ml. Total volume of cell suspension used in NMR experiment was 0.5-1.0 ml (packed volume). A time course of protein uptake was tested for each individual protein, to identify the best loading time with minimum cell toxicity and maximum protein loading. After incubation, cells were centrifuge gently at 500 rpm for 20 minutes and washed with 4×5 ml of DMEM. Each wash followed by gentle spin to remove the wash medium. After washing, the cells were resuspended into 1 ml of NMR sample buffer.

NMR sample buffer contains (1 ml): PBS 0.65 ml, DMEM 0.2 ml, 0.1 ml $D_2O$, 0.05 ml of 4% BSA, MG132 3 protease inhibitor 2 μl, antibiotics mixture 10 μl and cell culture vitamin 100× solution 10 μl. This step is critical for good NMR experiments, which should be very careful to make cell slurry as homogenous as possible to avoid any macroscopic clumps of cells. Any macroscopic clumps have to be removed before the NMR experiments. The cells were carefully transferred into a 5 mm NMR tube and let the cells settled for 10-30 minutes.

After NMR experiments, the cells were taken out from the NMR tube and the tube was washed with 2×3 ml NMR sample buffer. The cells were then used for several assays to test cell viability after NMR experiments. The results indicated the following results:

Cell viability was evaluated by MTT assay and trypan blue stain assay. For human apolipoprotein A-I loaded into Hela cells, MTT assay showed 70% cell viability for NMR sample after 24 hour NMR experiment at 30° C., as compared with the control that is the cells in the culture dish. The trypan blue stain assay indicated that >90% of cells were alive. For human apolipoprotein E loaded into Hela cells, the trypan blue stain assay indicated that >75% of cells were alive after 3-day NMR experiments at 30° C.

All NMR experiments were collected using a Varian 600 MHz NMR spectrometer with a cold probe. Primarily, $^1H$-$^{15}N$ HSQC experiments of several different proteins were collected, including human apolipoprotein AI (243-residues), human apolipoprotein E (299-residues) and mouse MESD (195-residues). These proteins are large proteins and triple-labeled protein samples were used.

Throughout this application, author and year, and patents, by number, reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

The invention claimed is:

1. A method of protein transduction into mammalian cells, the method comprising the steps of:
- modifying a protein to be introduced into a cell with a reagent that enables the protein to be efficiently delivered into mammalian cells, the reagent comprising: a cation reagent and a lipid in a carrier, wherein the cation reagent comprises polyethylenimine; thereby producing a non-covalently bound, dissociable complex of: the protein to be introduced into a cell, the cation reagent and the lipid; and
- delivering the non-covalently bound, dissociable complex into mammalian cells.

2. The method according to claim 1, further including the step of expressing the protein in bacteria prior to said modifying step.

3. The method according to claim 2, further including the step of in vivo labeling the proteins with the NMR-active isotopes during bacterial expression.

4. The method according to claim 1, further including the step of in vitro labeling the protein with small molecule fluorescence probes prior to modifying the protein.

5. The method according to claim 3, further including monitoring protein activity.

6. A composition for transduction of a protein into a cell, said composition comprising:
- a non-covalently bound, dissociable complex of:
- a protein to be introduced into a cell;
- a cation reagent, wherein the cation reagent comprises polyethylenimine; and
- a lipid in a carrier.

7. The composition according to claim 6, wherein said lipid is selected from the group consisting essentially of DOTAP, DOPE, POPC, and DMPE.

8. The composition according to claim 6, wherein said enhancer is an enhancer that enhances cell loading of the dissociable complex.

9. The composition according to claim 8, wherein said enhancer selected from the group consisting essentially of DMSO, MG132, $CaCl_2$ and growth factor.

10. The composition according to claim 6, further including at least one selected from the group consisting essentially of cell membrane surfactants, stabilizers, and other inert carriers.

11. A method of specific delivery of an exogenous protein into a target sub-cellular compartment, the method comprising the steps of:

modifying the exogenous protein with a composition according to claim 6, producing a non-covalently bound, dissociable complex of: the exogenous protein; a cation reagent; and a lipid in a carrier, wherein the cation reagent comprises polyethylenimine; and delivering the non-covalently bound, dissociable complex into mammalian cells.

12. A method of treating a protein to enable proper in cell folding by exposing the protein to the composition of claim 6 for enabling utilization of cell folding machinery of the mammalian cells.

13. A method of treating a protein to enable proper in cell post-translational modification by exposing the protein to the composition of claim 6 for enabling the utilization of cell post-translational modification machinery within mammalian cells.

14. A method of analyzing secretion pathways of exogenous proteins after being transduced into mammalian cells using fluorescence imaging by: forming a non-covalently bound, dissociable complex of the exogenous protein according to claim 6;

delivering the protein into mammalian cells; and analyzing the secretion pathway of the protein using fluorescence imaging.

* * * * *